United States Patent [19]
Chang

[11] Patent Number: 5,741,772
[45] Date of Patent: Apr. 21, 1998

[54] NEUROTROPHIC FACTOR NNT-1

[75] Inventor: Ming-shi Chang, Newbury Park, Calif.

[73] Assignee: Amgen Inc., Thousand Oaks, Calif.

[21] Appl. No.: 792,019

[22] Filed: Feb. 3, 1997

[51] Int. Cl.⁶ .......................... A01N 37/18; A61K 38/00
[52] U.S. Cl. .............................. 514/2; 530/300; 530/350
[58] Field of Search ................................ 530/300, 350; 514/2

[56] References Cited

PUBLICATIONS

Humpel, et al., *Science*, 269:552–554 [1995].
Isackson, *Current Opinions in Neurobiology* 5:50–357 [1995].
MacDonald and Hendrikson, *Cell*, 73:421–424 [1993].
Nedivi et al (*Nature*, 363:718–722 [1993].
Nedivi et al., *Proc. Natl. Acad. Sci USA*, 93:2048–2053 [1996].

*Primary Examiner*—Marian C. Knode
*Assistant Examiner*—Heather A. Bakalyar
*Attorney, Agent, or Firm*—Robert R. Cook; Ron K. Levy; Steven Odre

[57] ABSTRACT

Disclosed are nucleic acids encoding novel neurotrophic factors, designated NNT-1. Also disclosed are amino acid sequences for NNT-1 polypeptides, methods for preparing NNT-1 polypeptides, and other related aspects.

6 Claims, 14 Drawing Sheets

FIG. 1

```
  1  ATTAAAGCTT  CGCCGGAGCC  GCGGCTCGCC  CTCCCACTCC  GCCAGCCTCC
 51  GGGAGAGGAG  CCGCACCCGG  CCGGCCCAGC  CCCAGCCCCA  TGGACCTCCG
101  AGCAGGGGAC  TCGTGGGGGA  TGTTAGCGTG  CCTGTGCACG  GTGCTCTGGC
151  ACCTCCCTGC  AGTGCCAGCT  CTCAATCGCA  CAGGGGACCC  AGGGCCTGGC
201  CCCTCCATCC  AGAAAACCTA  TGACCTCACC  CGCTACCTGG  AGCACCAACT
251  CCGCAGCTTG  GCTGGGACCT  ATCTGAACTA  CCTGGGCCCC  CCTTTCAACG
301  AGCCAGACTT  CAACCCTCCC  CGCCTGGGGG  CAGAGACTCT  GCCCAGGGCC
351  ACTGTTGACT  TGGAGGTGTG  GCGAAGCCTC  AATGACAAAC  TGCGGCTGAC
401  CCAGAACTAC  GAGGCCTACA  GCCACCTTCT  GTGTTACTTG  CGTGGCCTCA
451  ACCGTCAGGC  TGCCACTGCT  GAGCTGCGCC  GCAGCCTGGC  CCACTTCTGC
501  ACCAGCCTCC  AGGGCCTGCT  GGGCAGCATT  GCGGGCGTCA  TGGCAGCTCT
551  GGGCTACCCA  CTGCCCCAGC  CGCTGCCTGG  GACTGAACCC  ACTTGGACTC
601  CTGGCCCTGC  CCACAGTGAC  TTCCTCCAGA  AGATGGACGA  CTTCTGGCTG
651  CTGAAGGAGC  TGCAGACCTG  GCTGTGGCGC  TCGGCCAAGG  ACTTCAACCG
701  GCTCAAGAAG  AAGATGCAGC  CTCCAGCAGC  TGCAGTCACC  CTGCACCTGG
751  GGCTCATGG   CTTCTGACTT  CTGACCTTCT  CCTCTTCGCT  CCCCCCC
```

FIG.2

Genomic sequences of the human NNT-1

```
  1  aacctgcgag tgggcctggc ggatgggatt attaaagctt cgccggagcc
 51  gcggctcgcc ctcccactcc gccagcctcc gggagaggag ccgcacccgg
101  ccggcccagc cccagccccA TGGACCTCCG AGCAGgt--- ----------

-----( >1 kb )-------------------------- tgaaaaccca 151  aactagccct gctcttcata acatgacaag cagcgcccca tctgatacct
201  aaaccgacca agtcacagcc ctccaactca ccctctgcct gcccagacct
251  caccacatcc ttgstggact caaacctcaa ccgcactaaa tcaaccaaat
301  cccaagtcta aactaatctg aaacttttaa agtaacccag tccttaaacc
351  taacctagcc caatgccaat tatatctacc ctagccaaac cctaactgcc
401  tttgccagtc caaagtgtcc actgaatcct caccttggtc ctcactgaaa
451  atcccagaaa agcatatttc cccactgccc acatccctcc ttacagcacc
501  caaccctggc ctctggactc ctggtatcct gggatgtcca aactctgcag
551  tgccatcagc caacaagccc gactcgtcaa atgcacctct ctccttcct
601  gtccccaccc ttgcaggctg atggaaaggc ctcattgaag tccaactttt
651  ccccacctaa caccaagaac ggggtgaacc tccacactgc caccgttccc
```

FIG.2A

```
 701   tgagagtgag cactaaatct ccttcaatct aaccccaccc tacacttccc
 751   acactcagga atcacatcct agaatatacc caaaactaag ccccataagg
 801   cagcccgacc ctagtggtct aaccctatac cttgcttcct atgggtgagt
 851   ctgttcttgg cggccgcctc tctcctgctt cctcccttag agctgactgt
 901   gctcagcctg ccagctctga catgtgctgt ctccaccct ctgactcccc
 951   tcaagctgca gtgggactgg aagactggca ggaagctagg gtacaactgg
1001   aacacaggca ggtcgacctg cagtccctag cctggcccc gtccctccat
1051   gtacacacat atacatgttg cacacacac agtggcacac atgccaaaga
1101   ctctctcagc tgacacacag atccattctc aagtatctac tgatagacac
1151   tcatgcgtgc caagtcctca cctcaaaaca tacacatgcc tctctttctc
1201   tcccgtcttg ccaggagtgt ttcccctcct ccatcccctc tgcctcccat
1251   ctggtgtccc accctcaccc cccacccagc caaggtggg gacagacacc
1301   tgagggctg ccagctgctt ccccgtgtgg gcccgggccg cgctcatgct
1351   tctcgtccat cctgcccaca gGGGACTCGT GGGGGATGTT AGCGTGCCTG
1401   TGCACGGTGC TCTGGCACCT CCCTGCAGTG CCAGCTCTCA ATCGCACAGG
1451   GGACCCAGGG CCTGGCCCCT CCATCCAGAA AACCTATGAC CTCACCCGCT
1501   ACCTGGAGCA CCAACTCCGC AGCTTGGCTG GGACCTATgt gagtatccag
1551   cgtaggaatc tgggagttgg ggaggagtga ggagttgggg aaagacagtc
1601   ctaaccgtgg agggttctgg taaatgatgg ggtgaggagg ggctctttgg
```

FIG.2B

```
1651  ctcccaccag tcccctgtc  tggtctatct cctgcccttc cctcttaggt 1701  ggcccccca  cttccccatc cctggcccca ggactaggca tgtgggcagg 1751  cctcgcaccc gccttggccc attgcccac  tggctgccag cccagccgcc 1801  cgcctccccc tgggggccgg ggaagtctcc tctgtttaca ccgtgttgtg 1851  gtgtctcttg cgcgggcggg gttgggtggg gacagagggg ccccacctcc 1901  catgcctgcg ttccagctcg cctctgcccc cagacctggg gccctgctgc 1951  tctggaccca ggggcctccc ttccgtctgc ctctcccatc ctagctgggc 2001  ctcctagggg ggtcatgggg aaggggact  gtagggaacc caggcagtag 2051  tggcaggggg tttagggtgt ggatggaggt tatgctgtaa ggatttgggg 2101  gtggtccaga ggtgttcaga gagcccagga gagaaggaag gagggttgga 2151  ggagccgagg caccatgggg aaccggcccc ctcttcccgt gttcctcttc 2201  cacatccag  accctactct ggagccaggg aaagaaaagg gaagaaggtg 2251  gcggggagc  tggctccagc cccaggatac accgaggaaa ttagtttgtc 2301  tctgtgcttg tcagcgtgtg aacctcccccc tgggcccttg cctatcccag 2351  gcctctcccc ttgcttctcc cttctttccc agttatacat ctccctcatc 2401  cctttccctg ggcccagcc  gctccccga  gggttggaaa gggctctgcc 2451  ctcttcccta taccatgctg tcttccatag ccttcctcct gtcctactca 2501  tgagactgcc tccatttctt ccttctgcaa ccctgctcct atcagctgaa
```

FIG. 2C

```
2551   cccttctttc ggagtgttag tgagtacccg tctctcccca gccctcagc
2601   tggtgggcct gggtgtgtca gcggcaaatg gggctctggt tccaatgggc
2651   cactctcatc tctctcttgt tccttgtgca gaaaacctt gcttcactcc
2701   actgccctct ctagttcccg accttttt tctcctggct ttccctgcca
2751   aatttctcca aggagtggtc tacacctct gcctccactt cctctccacc
2801   cactcacttc ttaaccccct gcaatctggc ttccaggccc cagcaatggt
2851   tctctccaag gtcgtcaggc acctccttgc caagcccgac agtgttttga
2901   aggctcattc tccttgctgt ctgttttgca gccacactgc tgagcgctgc
2951   tgccttctcg aactcctctt ccttggtctc tgcactctcc tgggccacct
3001   tctacctctc cagctcctcc aggctcctct tcctctctgt cctgccccca
3051   cagcgggcac tctcccaagg tttgcccacc cagccaatca gcacgtcctt
3101   cctgagcgtc ttgtgcgtct cctcctcctc cttttctac gcctctccat
3151   tggagagctc accaccgcca ctgcttcaac tgtcacctgc atacaaatga
3201   tatccttatt ggaaaaactc agggaggcca tgaacaaaga agcctagcat
3251   ggagacaggg ccagtgtcag gggacacaaa aaatagaaac tttgggagca
3301   ggtatctcct tggtggtgag ccagcggctc tgccctcctc cttccccatc
3351   accctctcct tttcacagCT GAACTACCTG GGCCCCCTT TCAACGAGCC
3401   AGACTTCAAC CCTCCCCGCC TGGGGGCAGA GACTCTGCCC AGGGCCACTG
3451   TTGACTTGGA GGTGTGGCGA AGCCTCAATG ACAAACTGCG GCTGACCCAG
```

FIG.2D

```
3501  AACTACGAGG CCTACAGCCA CCTTCTGTGT TACTTGCGTG GCCTCAACCG

3551  TCAGGCTGCC ACTGCTGAGC TGCGCCGCAG CCTGGCCCAC TTCTGCACCA

3601  GCCTCCAGGG CCTGCTGGGC AGCATTGCGG GCGTCATGGC AGCTCTGGGC

3651  TACCCACTGC CCAGCCGCT GCCTGGGACT GAACCCACTT GGACTCCTGG

3701  CCCTGCCCAC AGTGACTTCC TCCAGAAGAT GGACGACTTC TGGCTGCTGA

3751  AGGAGCTGCA GACCTGGCTG TGGCGCTCGG CCAAGGACTT CAACCGGCTC

3801  AAGAAGAAGA TGCAGCCTCC AGCAGCTGCA GTCACCCTGC ACCTGGGGGC

3851  TCATGGCTTC tgacttctga ccttctcctc ttcgctcccc cttcaaaccc 3901  tgctcccact tgtgagagc cagccctgta tgccaacacc tgttgagcca 3951  ggagacagaa gctgtgagcc tctggccctt tcctggaccg gctgggcgtg 4001  tgatgcgatc agccctgtct cctccccacc tcccaaaggt ctaccgagct 4051  ggggaggagg tacagtaggc cctgtcctgt cctgtttcta caggaagtca 4101  tgctcgaggg agtgtgaagt ggttcaggtt ggtgcagagg cgctcatggc 4151  ctcctgcttc ttgcctacca cttggccagt gcccacccag ccctcaggt 4201  ggcacatctg gagggcaggg gttgaggggc caccaccaca catgcctttc 4251  tggggtgaag ccctttggct gccccactct ccttggatgg gtgttgctcc
```

FIG.2E

```
4301  cttatcccca aatcactcta tacatccaat tcaggaaaca aacatggtgg 4351  caattctaca caaaaagaga tgagattaac agtgcagggt tggggtctgc 4401  attggaggtg ccctataaac cagaagagaa aatactgaaa gcacaggggc 4451  aggacagac cagaccagac ccaggagtct ccaaagcaca gagtggcaaa 4501  caaaacccga gctgagcatc aggaccttgc ctcgaattgt cttccagtat 4551  tacggtgcct cttctctgcc ccctttccca gggtatctgt gggttgccag 4601  gctggggagg gcaaccatag ccacaccaca ggatttcctg aaagtttaca 4651  atgcagtagc attttggggt gtagggtggc agctccccaa ggccctgccc 4701  cccagcccca cccactcatg actctaagtg tgttgtatta atatttattt 4751  atttggagat gttatttatt agatgatatt tattgcagaa tttctattct 4801  tgtattaaca aataaaatgc ttgccccaga acttagtctc tttgcccagc 4851  ctcacccctc ctggtgctca tcagactctt gccacccctg gctcccactc 4901  cctgcttgcc tctggtggag ctgcacagag ctctgggaag aggccctctt 4951  cctccccgca ctggggcgat gggcgcacct cagacttacc cactgctgct 5001  gccaccacca accccttgat ccctcagtcc tcccacacag cttctgtcca 5051  ccccaggttt ccctcacccc acctttgcta agtcttcctc a
```

FIG.3

```
       -27                                  1
        MDLR AGDSWGMLAC LCTVLWHLPA VPALNRTGDP GPGPSIQKTY    17

DLTRYLEHQL RSLAGTYLNY LGPPFNEPDF NPPRLGAETL PRATVDLEVW    67

RSLNDKLRLT QNYEAYSHLL CYLRGLNRQA ATAELRRSLA HFCTSLQGLL   117

GSIAGVMAAL GYPLPQPLPG TEPTWTPGPA HSDFLQKMDD FWLLKELQTW   167
                                 198
LWRSAKDFNR LKKKMQPPAA AVTLHLGAHG F*                      198
```

FIG.4

```
  1  TATTATTAAA GCTTCGCCGG AGCCGCGGCT CGCCCTCCCA CTCCGCCAGC
 51  CTCTGGGAGA GGAGCCGCGC CCGGCCGGCC CGGCCCCAG CCCCATGGAC
101  CTCCGAGCAG GGGACTCGTG GGGGATGTTA GCTTGCCTAT GCACGGTGCT
151  GTGGCACCTC CCTGCAGTGC CAGCTCTTAA TCGCACAGGA GATCCAGGCC
201  CTGGCCCCTC CATCCAGAAA ACCTATGACC TCACCCGCTA CCTGGAGCAT
251  CAACTCCGCA GCTTAGCTGG GACCTACCTG AACTACCTGG GGCCCCCTTT
301  CAACGAGCCT GACTTCAATC CTCCTCGACT GGGGGCAGAA ACTCTGCCCA
351  GGGCCACGGT CAACTTGGAA GTGTGGCGAA GCCTCAATGA CAGGCTGCGG
401  CTGACCCAGA ACTATGAGGC GTACAGTCAC CTCCTGTGTT ACTTGCGTGG
451  CCTCAACCGT CAGGCTGCCA CAGCTGAACT CCGACGTAGC CTGGCCCACT
501  TCTGTACCAG CCTCCAGGGC CTGCTGGGCA GCATTGCAGG TGTCATGGCG
551  ACGCTTGGCT ACCCACTGCC CCAGCCTCTG CCAGGGACTG AGCCAGCCTG
601  GGCCCCTGGC CCTGCCCACA GTGACTTCCT CCAGAAGATG GATGACTTCT
651  GGCTGCTGAA GGAGCTGCAG ACCTGGCTAT GGCGTTCAGC CAAGGACTTC
701  AACCGGCTTA AGAAGAAGAT GCAGCCTCCA GCAGCTTCAG TCACCCTGCA
751  CTTGGAGGCA CATGGTTTCT GACCTCTGAC CCTTAACCCC CACACCTCCA
801  GGCCCAGTCA GCTGTGCTT
```

FIG. 5

```
-27                                   1
MDLRAGDSWG MLACLCTVLW HLPAVPALNR TGDPGPGPSI QKTYDLTRYL    23

EHQLRSLAGT YLNYLGPPFN EPDFNPPRLG AETLPRATVN LEVWRSLNDR    73

LRLTQNYEAY SHLLCYLRGL NRQAATAELR RSLAHFCTSL QGLLGSIAGV   123

MATLGYPLPQ PLPGTEPAWA PGPAHSDFLQ KMDDFWLLKE LQTWLWRSAK   173
                           198
DFNRLKKKMQ PPAASVTLHL EAHGF*                             198
```

FIG.6

```
                        1                                                                50
          NNT-1         ..........  ..........  .           MDL  RAGDSWGMLA  CLCTVLWHLP
          Il-11         ..........  ..........  ..........       MNCVCRLVLV  VLS..LWPDT
           Il-6         .           MNSFSTSAF    GPVAFSLGLL      LVLPAAFPAP
           GCSF         ..........  ..........  ....MAGPAT  QSPMKLMALQ  LLL...WHSA
   Cardiotrophin        ..........  ..........  ..........  ....             MSRREG
           CNTF         ..........  ..........  ..........  ..........  ....MAFTEH
      Oncostatin        ..........  ..........  ..........  ..MGVLLTQR  TLLSLVLALL
            LIF         ..........              MKVLAAGVVP  LLLVLHWKHG 51                                                               100
          NNT-1         AVPALNRTG.  ....DPGPGPS  IQKTYDLTRY  LEHQLRSLAG  TYLNYLGPPF
          Il-11         AVAPGPPPGP  PRVSPDPRAE   LDSTVLLTRS  LLADTRQLAA  QLRDKFPA..
           Il-6         VPPGEDSKDV  AAPHRQPLTS   SERIDKQIRY  ILDGISALRK  ETCN......
           GCSF         LWTVQEATPL  GPASSLPQSF   LLKCLEQVRK  IQGDGAALQE  KLCA......
   Cardiotrophin        SLEDPQTDSS  VSLLPHLEAK   IRQTHSLAHL  LTKYAEQLLQ  EYVQLQGDPF
           CNTF         S.........  .PLTPHRRDL   CSRSIWLARK  IRSDLTALTE  SYVKHQGLNK
      Oncostatin        FPSMASMAAI  GSCSKEYRVL   LGQLKQTD.   LMQDTSRLLD  PYIRIQGLDV
            LIF         AGSPLPITPV  NATCAIRHPC   HNNLMNQIRS  QLAQLNGSAN  AL........

101                                                              150
          NNT-1         NEPDFNPPRL  GAETLPRATV   DLEVWRSLND  KLRLTQN..Y  EAY.SHLLCY
          Il-11         .DGDHNLDSL  PTLAMSAGAL   GALQLPGVLT  RLR.......  ....ADLLSY
           Il-6         ...KSNMCES  SKEALAENNL   NLPKMAEKDG  CFQSGFN..E  ETCLVKIITG
           GCSF         ...TYKLCHP  EELVLLGHSL   GIPW.APLSS  CPSQALQ..L  AGCLSQLHSG
   Cardiotrophin        ...GLPSFSP  PRLPVAGLSA   PAPSHAGLPV  HERLRLD..A  AALAALPPLL
           CNTF         ...NINLDSA  DGMPVAS...   .TDQWSELTE  AERLQEN..L  QAYRTFHVLL
      Oncostatin        PKLREHCRER  PGAFPSEETL   RGLGRRGFLQ  TLNATLGCVL  HRLADLEQRL
            LIF         ....FILYYT  AQGEPFPNNL   DKLCGPNVTD  FPPFHANGTE  KAKLVELYRI 151                                                              200
          NNT-1         LRGLN..RQA  ATAELR...R   SLAHFCTSLQ  GLLGSIAGVM  AAL..GYP.L
          Il-11         LRHVQWLRRA  GGSSLKTLEP   ELGTLQARLD  RLLRRLQLLM  SRL..ALP.Q
           Il-6         LLEFEVYLEY  LQNRFESSEE   QARAVQMSTK  VLIQFLQKKA  KNL..DAI.T
           GCSF         LFLYQGLLQA  LEGISPELGP   TLDTLQLDVA  DFATTIWQQM  EEL..GMA.P
   Cardiotrophin        D.AVCRRQAE  LNPRAPRLLR   RLEDAARQAR  ALGAAVEALL  AAL..GAANR
           CNTF         ARLLEDQQVH  FTPTEGDFHQ   AIHTLLLQVA  AFAYQIEELM  ILL..E..YK
      Oncostatin        PKAQDLERSG  LNIEDLEKLQ   MARPNILGLR  NNIYCMAQLL  DNS..DTAEP
            LIF         VVYLGTSLGN  ITRDQKILNP   SALSLHSKLN  ATADILRGLL  SNVLCRLCSK
```

FIG.6A

```
                   201                                                      250
        NNT-1   PQPLPGTEPT WTPGPAHSDF LQKMDDFWLL KELQTWLWRS AKDFNR..LK
        Il-11   PPPDPPAPPL APPSSAWGGI ...RAAHAIL GGLHLTLDWA VRGLLL..LK
         Il-6   TPDPTTNASL LTKLQAQNQW LQDMTTHLIL RSFKEFLQSS LRALRQ..M*
         GCSF   ALQPTQGA.. MPAFASAFQR RAG..GVLVA SHLQSFLEVS YRVLRH..LA
 Cardiotrophin   GPRAEPPAAT ASAASATGVF PAKVLGLRVC GLYREWLSRT EGDLGQ..LL
         CNTF   IPRNEADGMP INVGDG.GLF EKKLWGLKVL QELSQWTVRS IHDLRF..IS
    Oncostatin   TKAGRGASQP PTPTPASDAF QRKLEGCRFL HGYHRFMHSV GRVFSK..WG
          LIF   YHVGHVDVTY GPDTSGKDVF QKKKLGCQLL GKYKQIIAVL AQAF*

251                                                      300
        NNT-1   KKMQPPAAAV TLHLGAHGF* .......... ..........
        Il-11   TRL*...... .......... .......... .......... ......
         Il-6
         GCSF   QP*....... .......... .......... .......... ......
 Cardiotrophin   .PGGSA*
         CNTF   .SHQTGIPAR GSHYIANNKK M*.. .......... ..........
    Oncostatin   ESPNRSRRHS PHQALRKGVR RTRPSRKGKR LMTRGQLPR*. ..........
          LIF
```

NEUROTROPHIC FACTOR NNT-1

BACKGROUND

1. Field of the Invention

This invention relates to a novel polypeptide designated NNT-1 and related polypeptides that have neurotrophic activity, to novel nucleic acid molecules encoding such polypeptides, and to other related aspects.

2. Description of Related Art

A number of neurological disorders and diseases are caused at least in part by degeneration or death of particular classes of neurons. For example, Parkinson's disease is characterized by slowing of voluntary muscle movement, muscular rigidity, and tremor. Such symptoms are attributed at least in part to progressive degeneration of dopamine-producing neurons located in a specific region of the brain called the substantia nigra. Degeneration of these neurons ("dopaminergic neurons") results in a decrease of dopamine levels in an adjacent region of the brain called the striatum. The striatum contains neurons expressing receptors for dopamine; these neurons are involved in the control of motor activity. The cause of the degeneration of dopaminergic neurons is unknown, but has been attributed to free radicals, excess iron content, environmental toxins, excitatory amino acid neurotoxicity, and possibly a deficiency of certain neurotrophic factors (Jenner, Neurology, Suppl. 3:S6–S12 [1995]; Adams and Victor, eds. *Principles of Neurology*, Chapter 42: Degenerative Diseases of the Nervous System, McGraw Hill, N.Y. [1993]).

Diseases such as amyotrophic lateral sclerosis (ALS; also known as Lou Gehrig's disease), progressive muscular atrophy, and hereditary motor and sensory neuropathy (Charcot-Marie-Tooth disease) all result at least in part from a decay of motor neurons which are located in the ventral horn of the spinal cord.

The hippocampus, a well defined structure that is part of the cerebral cortex of the brain, is important in the formation of long term memory. Destruction of the hippocampus, for example by ischemia, can result in an inability to form new memories. Degeneration of pyramidal CA1 neurons, which are located in the CA1 region of the hippocampus, is one characteristic of Alzheimer's disease. These same neurons are selectively vulnerable to ischemic and anoxic damage which occur in conditions such as stroke and head trauma. In addition, the CA1 pyramidal hippocampal neurons as well as pyramidal neurons located in the CA3 region of the hippocampus, are selectively injured in epilepsy.

The striatum is the innervation region of the nerve terminals of dopaminergic-containing neurons from the substantia nigra. The majority of striatal neurons utilize GABA (4-aminobutyric acid) as their neurotransmitter. The striatum is the major target of the progressive neurodegeneration that occurs in Huntington's disease, in which the major neuron loss is that of the striatal GABA-utilizing neurons.

The serotonin-containing neurons are located in groups clustered around the midline of the hindbrain. These neurons are involved in the control of body temperature, mood, and sleep. Disorders of the serotonin-containing neuron system include, for example, depression, other mood disorders, and sleep disturbances.

Photoreceptor cells are a specialized subset of retina neurons, and are responsible for vision. Injury and/or death of photoreceptor cells can lead to blindness. Degeneration of the retina, such as by retinitis pigmentosa, age-related macular degeneration, and stationary night blindness, are all characterized by the progressive atrophy and loss of function of photoreceptor outer segments which are specialized structures containing the visual pigments that transform a light stimulus into electrical activity.

While there are some therapies available to treat the symptoms and decrease the severity of such diseases (e.g., L-dopa to treat Parkinson's disease), there currently exists no effective treatment to prevent or reduce the degeneration of most of the above mentioned classes of affected neurons, or to promote their repair.

Recently, several naturally occurring proteinaceous molecules have been identified based on their trophic activity on various neurons. These molecules are termed "neurotrophic factors". Neurotrophic factors are endogenous, soluble proteins that can stimulate or regulate survival, growth, and/or morphological plasticity of neurons (see Fallon and Laughlin, *Neurotrophic Factors*, Academic Press, San Diego, Calif. [1993]).

The known neurotrophic factors belong to several different protein superfamilies of polypeptide growth factors based on their amino acid sequence homology and/or their three-dimensional structure (MacDonald and Hendrikson, *Cell*, 73:421–424 [1993]). One family of neurotrophic factors is the neurotrophin family. This family currently consists of NGF (nerve growth factor), BDNF (brain derived neurotrophic factor), NT-3 (neurotrophin-3), NT-4 (neurotrophin-4), and NT-6 (neurotrophin-6).

CNTF (ciliary neurotrophic factor) and LIF (leukemia inhibitory factor) are cytokine polypeptides that have neurotrophic activity. By virtue of their structural features and receptor components, these polypeptides are related to a family of hematopoietic cytokines that includes IL-6 (interleukin-6), IL-11 (interleukin-11), G-CSF (granulocyte-colony stimulating factor), and oncostatin-M. NNT-1 of the present invention exhibits significant similarity to various members of this family of neurotrophic factors. See FIG. 6.

GDNF (glial derived neurotrophic factor) is a neurotrophic factor that belongs to the TGF-beta (transforming growth factor beta) superfamily. GDNF displays potent survival and differentiation-promoting actions for dopaminergic and motor neurons (Lin et al., *Science*, 260:1130–1132 [1993]; Yan et al., *Nature*, 373:341–344 [1995]).

While these neurotrophic factors are known to increase growth and/or survival of neurons, there is less known about the molecules that work in conjunction with these factors. One manner in which additional neurotrophins and related molecules may be identified is to administer to an animal one or more compounds known to have an effect on the nervous system, and to then analyze tissues for the induction of genes involved in neural responses to the compounds. For example, one can screen for genes that are induced in certain tissues of the nervous system, such as the hippocampal region of the brain. This technique was used by Nedivi et al (*Nature*, 363:718–722 [1993]; Nedivi et al., *Proc. Natl. Acad. Sci USA*, 93:2048–2053 [1996]) to identify novel genes that are induced in the dentate gyrus portion of the hippocampus in response to administration of a neurotransmitter analog of glutamate called kainate (kainic acid).

Expression of many neurotrophic factors such as NGF, BDNF, NT3, GDNF, bFGF, IGF-1 and TGF-beta is regulated by afferent neuronal activity and/or by neuronal injury. Strong induction of some of these genes can be observed in the hippocampus dentate gyrus in response to the glutamate analog kainate (Isackson, *Current Opinions in Neurobiology* 5:50–357 [1995]). Kainate treatment appears to increase the release of novel compounds from the hippocampus of alert rats, and this activity appears to be different from the actions of known neurotrophic factors (Humpel, et al., *Science*, 269:552-554 [1995]).

In view of the fact that many nervous system disorders and diseases have no known cure, there is a need in the art to identify novel compounds for treating neurological conditions and diseases such as Parkinson's disease, amyotrophic lateral sclerosis (ALS), Alzheimer's disease, stroke, and various degenerative disorders that affect vision.

Accordingly, it is an object of the present invention to provide novel compounds that may be useful in promoting neuron regeneration and restoring neural functions.

It is a further object of the invention to provide a method of treating neurological diseases such as those set forth herein.

These and other objects will be apparent to one of ordinary skill in the art from the present disclosure.

SUMMARY OF THE INVENTION

In one embodiment, the present invention provides a nucleic acid molecule encoding a polypeptide selected from the group consisting of:

(a) the nucleic acid molecule of SEQ ID NO:1;

(b) the nucleic acid molecule of SEQ ID NO:3;

(c) a nucleic acid molecule encoding the polypeptide of SEQ ID NO:2 or a biologically active fragment thereof;

(d) a nucleic acid molecule that encodes a polypeptide that is at least 70 percent identical to the polypeptide of SEQ ID NO:2;

(e) a nucleic acid molecule that hybridizes under stringent conditions to any of (a)–(d) above; and (f) a nucleic acid molecule that is the complement of any of (a)–(e) above.

In another embodiment, the present invention provides a nucleic acid molecule encoding a polypeptide selected from the group consisting of:

(a') the nucleic acid molecule of SEQ ID NO:4;

(b') a nucleic acid molecule encoding the polypeptide of SEQ ID NO:5 or a biologically active fragment thereof;

(c') a nucleic acid molecule that encodes a polypeptide that is at least 70 percent identical to the polypeptide of SEQ ID NO:5;

(d') a nucleic acid molecule that hybridizes under stringent conditions to any of (a')–(c') above; and (e') a nucleic acid molecule that is the complement of any of (a')–(d') above.

In another embodiment, the invention provides vectors comprising these nucleic acid molecules, and host cells, either prokaryotic or eukaryotic, comprising the vectors.

The invention further provides an NNT-1 polypeptide selected from the group consisting of:

(a) the polypeptide of SEQ ID NO:2;

(b) the polypeptide that is amino acids 1–198 of SEQ ID NO:2;

(c) a polypeptide that is at least 70 percent identical to the polypeptide of (a) or (b); and (d) a biologically active fragment of any of (a)–(c).

The invention further provides an NNT-1 polypeptide selected from the group consisting of:

(a') the polypeptide of SEQ ID NO:5;

(b') the polypeptide that is amino acids 1–198 of SEQ ID NO:5;

(c') a polypeptide that is at least 70 percent identical to the polypeptide of (a') or (b'); and (d') a biologically active fragment of any of (a')–(c').

Optionally, the NNT-1 polypeptide may or may not have an amino terminal methionine.

In another embodiment, the invention provides a process for producing an NNT-1 polypeptide, wherein the polypeptide may be SEQ ID NO:2 or SEQ ID NO:5, amino acids 1–198 of SEQ ID NO:2, amino acids 1–198 of SEQ ID NO:5, or a biologically active fragment thereof, and wherein the process comprises:

(a) expressing a polypeptide encoded by an NNT-1 nucleic acid molecule in a suitable host; and (b) isolating the polypeptide.

The invention further provides anti-NNT-1 antibodies.

BRIEF DESCRIPTION OF THE DRAWINGS

FIG. 1 depicts the nucleic acid sequence of the cDNA encoding human NNT-1 (SEQ ID NO:1).

FIG. 2 depicts the nucleic acid sequence of the human genomic DNA for NNT-1 (SEQ ID NO:3).

FIG. 3 depicts the amino acid sequence for human NNT-1 (SEQ ID NO:1) as translated from the cDNA (SEQ ID NO:2). The first 27 amino acids may represent a signal peptide sequence, such that the mature form of NNT-1 starts at the leucine indicated as number 1. The * indicates the stop codon.

FIG. 4 depicts the nucleic acid sequence of the cDNA encoding murine NNT-1 (SEQ ID NO:4).

FIG. 5 depicts the amino acid sequence for murine NNT-1 (SEQ ID NO:5) as translated from the cDNA (SEQ ID NO:4). The first 27 amino acids may represent a signal peptide sequence, such that the mature form of murine NNT-1 starts at the leucine indicated as number 1. The * indicates the stop codon.

FIG. 6 depicts a comparison of amino acid sequences of NNT-1, IL-11 (SEQ ID NO:8), IL-6 (SEQ ID NO:9), G-CSF (SEQ ID NO:10), cardiotrophin (SEQ ID NO:11), CNTF (SEQ ID NO:12), oncostatin (SEQ ID NO:13), and LIF (SEQ ID NO:14). In each case, the human molecule is compared.

DETAILED DESCRIPTION OF THE INVENTION

Figure 7:
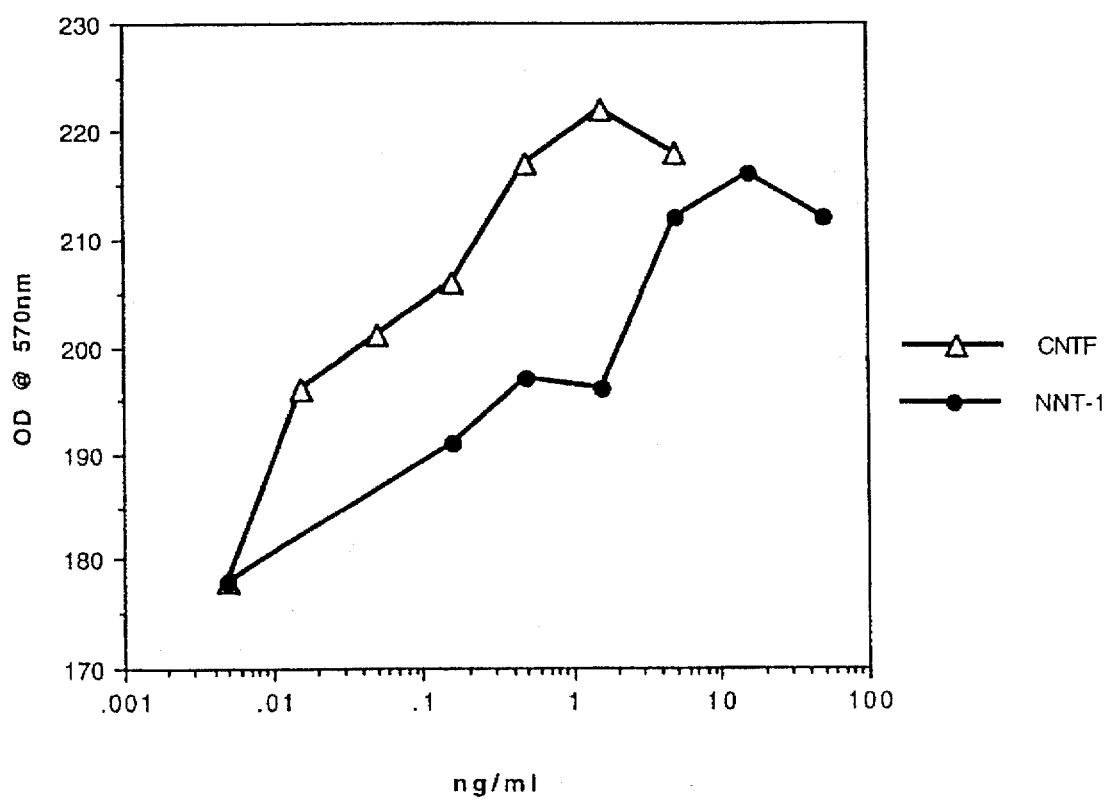
FIG. 7 depicts a graph of the results of a chick motor neuron activity assay for human NNT-1 compared to human CNTF.

Included in the scope of this invention are NNT-1 polypeptides such as the polypeptides of SEQ ID NO:2 or SEQ ID NO:5, and related biologically active polypeptide fragments and derivatives thereof. Further included within the scope of the present invention are nucleic acid molecules that encode these polypeptides, and methods for preparing the polypeptides.

I. NNT-1 Proteins/Polypeptides, Fragments and Derivatives Thereof

The term "NNT-1 protein" or "NNT-1 polypeptide" as used herein refers to any protein or polypeptide having the properties described herein for NNT-1. The NNT-1 polypeptide may or may not have an amino terminal methionine, depending, for example, on the manner in which it is prepared. By way of illustration, NNT-1 protein or NNT-1 polypeptide refers to:

(1) an amino acid sequence encoded by NNT-1 nucleic acid molecules as defined in any of the following items:

(a) the nucleic acid molecule of SEQ ID NO:1;
(b) the nucleic acid molecule of SEQ ID NO:3;
(c) a nucleic acid molecule encoding the polypeptide of SEQ ID NO:2 or a biologically active fragment thereof;
(d) a nucleic acid molecule that encodes a polypeptide that is at least 70 percent identical to the polypeptide of SEQ ID NO:2;
(e) a nucleic acid molecule that hybridizes under stringent conditions to any of (a)–(d) above; and
(f) a nucleic acid molecule that is the complement of any of (a)–(e) above; and
(a') the nucleic acid molecule of SEQ ID NO:4;
(b') a nucleic acid molecule encoding the polypeptide of SEQ ID NO:5 or a biologically active fragment thereof;
(c') a nucleic acid molecule that encodes a polypeptide that is at least 70 percent identical to the polypeptide of SEQ ID NO:5;
(d') a nucleic acid molecule that hybridizes under stringent conditions to any of (a')–(c') above; and
(e') a nucleic acid molecule that is the complement of any of (a')–(d') above; and
(2) naturally occurring allelic variants of the NNT-1 gene which result in one or more amino acid substitutions, deletions, and/or insertions as compared to the NNT-1 polypeptide of SEQ ID NO:2 or SEQ ID NO:5, and/or
(3) chemically modified derivatives as well as nucleic acid and or amino acid sequence variants thereof as provided for herein.

The NNT-1 polypeptides that have use in practicing the present invention may be naturally occurring full length polypeptides, or truncated polypeptides or peptides (i.e, "fragments").

The polypeptides may be in mature form or they may be attached to a native or heterogeneous signal peptide. For example, human and murine NNT-1 have signal peptides of amino acids −27 to −1 of SEQ ID NOS:2 and 5, respectively.

The polypeptides or fragments may be chemically modified, i.e., glycosylated, phosphorylated, and/or linked to a polymer, as described below, and they may have an amino terminal methionine, depending on how they are prepared. In addition, the polypeptides or fragments may be variants of the naturally occurring NNT-1 polypeptide (i.e., may contain one or more amino acid deletions, insertions, and/or substitutions as compared with naturally occurring NNT-1).

As used herein, the term "NNT-1 fragment" refers to a peptide or polypeptide that is less than the full length amino acid sequence of naturally occurring NNT-1 protein but has qualitatively a substantially similar type of biological activity as NNT-1 polypeptide or NNT-1 protein described above. Such a fragment may be truncated at the amino terminus, the carboxy terminus, or both, and may be chemically modified. Such NNT-1 fragments may be prepared with or without an amino terminal methionine. The activity of the fragments may be greater than, the same as, or less than the full-length (mature) NNT-1 polypeptide. Preferably, the activity of the fragment is $\geq 50\%$, more preferably $\geq 65\%$, most preferably $\geq 80\%$, of the activity of the full-length polypeptide, as measured by a standard activity assay, such as those set forth in the Examples section herein. Some exemplary fragments of this invention include the polypeptides wherein from 1 to 20 amino acids are removed from either the C-terminus, the N-terminus, or both termini, of the NNT-1 polypeptide.

As used herein, the term "NNT-1 derivative" or "NNT-1 variant" refers to an NNT-1 polypeptide, protein, or fragment that 1) has been chemically modified, as for example, by addition of one or more polyethylene glycol molecules, sugars, phosphates, or other such molecules not naturally attached to wild-type NNT-1 polypeptide, and/or 2) contains one or more nucleic acid or amino acid sequence substitutions, deletions, and/or insertions as compared to the NNT-1 amino acid sequence set forth in FIG. 3 (human) or FIG. 5 (murine).

As used herein, the terms "biologically active polypeptide" and "biologically active fragment" refer to a peptide or polypeptide in accordance with the above description for NNT-1 wherein the NNT-1 acts as a growth factor for neurons (e.g., motor neurons and/or sympathetic neurons).

Fragments and/or derivatives of NNT-1 that are not themselves active in activity assays may be useful as modulators (e.g., inhibitors or stimulants) of the NNT-1 receptors in vitro or in vivo, or to prepare antibodies to NNT-1 polypeptides.

The amino acid variants of NNT-1 of this invention preferably are at least 70% identical to either SEQ ID NO:2 or SEQ ID NO:5, more preferably at least about 80% identical, even more preferably at least about 90% identical.

Percent sequence identity can be determined by standard methods that are commonly used to compare the similarity in position of the amino acids of two polypeptides. By way of example, using a computer program such as BLAST or FASTA, the two polypeptides for which the percent sequence identity is to be determined are aligned for optimal matching of their respective amino acids (the "matched span", which can include the full length of one or both sequences, or a predetermined portion of one or both sequences). Each computer program provides a "default" opening penalty and a "default" gap penalty, and a scoring matrix such as PAM 250. A standard scoring matrix (see Dayhoff et al., in: Atlas of Protein Sequence and Structure, vol. 5, supp.3 [1978]) can be used in conjunction with the computer program. The percent identity can then be calculated using an algorithm contained in a program such as FASTA as:

$$\frac{\text{Total number of identical matches}}{[\text{length of the longer sequence within the matched span}] + [\text{number of gaps introduced into the longer sequence in order to align the two sequences}]} \times 100$$

Polypeptides that are at least 70 percent identical will typically have one or more amino acid substitutions, deletions, and/or insertions as compared with wild type NNT-1. Usually, the substitutions will be conservative so as to have little or no effect on the overall net charge, polarity, or hydrophobicity of the protein but optionally may increase the activity of NNT-1. Conservative substitutions are set forth in Table I below.

TABLE I

| Conservative amino acid substitutions | |
|---|---|
| Basic: | arginine |
|  | lysine |
|  | histidine |
| Acidic: | glutamic acid |
|  | aspartic acid |
| Polar: | glutamine |
|  | asparagine |

TABLE I-continued

Conservative amino acid substitutions

| | |
|---|---|
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The invention also encompasses species homologs of NNT-1; for example, NNT-1 homologs from a mammalian species such as dog, cat, mouse, rat, monkey, horse, pig, goat, rabbit, sheep and the like is contemplated in addition to human. The sequences of murine cDNA and protein are provided as SEQ ID NOS:4 and 5.

The invention further encompasses chimeric polypeptides, such as NNT-1 attached to all or a portion of another polypeptide. Preferably the chimeric polypeptide comprises NNT-1 attached to all or a portion of another neurotrophic factor, such as BDNF, GDNF, NT-3, NT-4, NT-5, NT-6, and the like. The polypeptides may be attached N to C terminus, C to C terminus, or N to N terminus.

II. Nucleic Acids

As used herein, the term "NNT-1" when used to describe a nucleic acid molecule refers to a nucleic acid molecule or fragment thereof, as set forth above.

The term "stringent conditions" refers to hybridization and washing under conditions that permit only binding of a nucleic acid molecule such as an oligonucleotide or cDNA molecule probe to highly homologous sequences. One stringent wash solution is 0.015M NaCl, 0.005M NaCitrate, and 0.1 percent SDS used at a temperature of 55° C.–65° C. Another stringent wash solution is 0.2×SSC and 0.1 percent SDS used at a temperature of between 50° C.–65° C. Where oligonucleotide probes are used to screen cDNA or genomic libraries, the following stringent washing conditions may be used. One protocol uses 6×SSC with 0.05 percent sodium pyrophosphate at a temperature of 35° C.–62° C., depending on the length of the oligonucleotide probe. For example, 14 base pair probes are washed at 35°–40° C., 17 base pair probes are washed at 45°–50° C., 20 base pair probes are washed at 52°–57° C., and 23 base pair probes are washed at 57°–63° C. The temperature can be increased 2°–3° C. where the background non-specific binding appears high. A second protocol utilizes tetramethylammonium chloride (TMAC) for washing oligonucleotide probes. One stringent washing solution is 3M TMAC, 50 mM Tris-HCl, pH 8.0, and 0.2 percent SDS. The washing temperature using this solution is a function of the length of the probe. For example, a 17 base pair probe is washed at about 45°–50° C.

NNT-1 nucleic acid molecules, fragments, and/or derivatives that do not themselves encode polypeptides that are active in activity assays may be useful as hybridization probes in diagnostic assays to test, either qualitatively or quantitatively, for the presence of NNT-1 DNA or RNA in mammalian tissue or bodily fluid samples.

NNT-1 nucleic acid molecules encoding NNT-1 polypeptides attached to native or heterogeneous signal peptides and/or to chimeric polypeptides as described herein above are also included within the scope of this invention.

III. Methods for Preparing NNT-1 Polypeptides

A. Recombinant Methods

The full length NNT-1 polypeptide or fragment thereof can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds, (*Current Protocols in Molecular Biology*, Green Publishers Inc. and Wiley and Sons, N.Y. [1994]). A gene or cDNA encoding the NNT-1 protein or fragment thereof may be obtained for example by screening a genomic or cDNA library, or by PCR amplification. Alternatively, a gene encoding the NNT-1 polypeptide or fragment may be prepared by chemical synthesis using methods well known to the skilled artisan such as those described by Engels et al.(Angew. *Chem. Intl. Ed.*, 28:716–734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the NNT-1 polypeptide will be several hundred nucleotides in length. Nucleic acids larger than about 100 nucleotides can be synthesized as several fragments using these methods. The fragments can then be ligated together to form the full length NNT-1 polypeptide. Usually, the DNA fragment encoding the amino terminus of the polypeptide will have an ATG, which encodes a methionine residue. This methionine may or may not be present on the mature form of the NNT-1 polypeptide, depending on whether the polypeptide produced in the host cell is secreted from that cell.

In some cases, it may be desirable to prepare nucleic acid and/or amino acid variants of naturally occurring NNT-1. Nucleic acid variants (wherein one or more nucleotides are designed to differ from the wild-type or naturally occurring NNT-1) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce NNT-1. Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s) on NNT-1, or those designed to delete an existing glycosylation and/or phosphorylation site(s) on NNT-1.

The NNT-1 gene or cDNA can be inserted into an appropriate expression vector for expression in a host cell. The vector is selected to be functional in the particular host cell employed (i.e., the vector is compatible with the host cell machinery such that amplification of the NNT-1 gene and/or expression of the gene can occur). The NNT-1 polypeptide or fragment thereof may be amplified/expressed in prokaryotic, yeast, insect (baculovirus systems) and/or eukaryotic host cells. Selection of the host cell will depend at least in part on whether the NNT-1 polypeptide or fragment thereof is to be glycosylated. If so, yeast, insect, or mammalian host cells are preferable; yeast cells will glycosylate the polypeptide, and insect and mammalian cells can glycosylate and/or phosphorylate the polypeptide as it naturally occurs on the NNT-1 polypeptide (i.e., "native" glycosylation and/or phosphorylation).

Typically, the vectors used in any of the host cells will contain 5' flanking sequence (also referred to as a "promoter") and other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide sequence located at the 5' or 3' end of the NNT-1 coding sequence that encodes polyHis (such as hexaHis) or another small immunogenic sequence. This tag will be expressed along with the protein, and can serve as an affinity tag for purification of the NNT-1 polypeptide from the host cell. Optionally, the tag can subsequently be removed from the purified NNT-1 polypeptide by various means such as using a selected peptidase for example.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native NNT-1 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the NNT-1 5' flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the NNT-1 polypeptide. If the vector of choice does not contain an origin of replication site, one may be chemically synthesized based on a known sequence, and ligated into the vector.

The transcription termination element is typically located 3' of the end of the NNT-1 polypeptide coding sequence and serves to terminate transcription of the NNT-1 polypeptide. Usually, the transcription termination element in prokaryotic cells is a G—C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is necessary for translation initiation of mRNA. The element is typically located 3' to the promoter and 5' to the coding sequence of the NNT-1 polypeptide to be synthesized. The Shine-Dalgarno sequence is varied but is typically a polypurine (i.e., having a high A—G content). Many Shine-Dalgarno sequences have been identified, each of which can be readily synthesized using methods set forth above and used in a prokaryotic vector.

In those cases where it is desirable for NNT-1 to be secreted from the host cell, a signal sequence may be used to direct the NNT-1 polypeptide out of the host cell where it is synthesized, and the carboxy-terminal part of the protein may be deleted in order to prevent membrane anchoring. Typically, the signal sequence is positioned in the coding region of NNT-1 nucleic acid sequence, or directly at the 5' end of the NNT-1 coding region. Many signal sequences have been identified, and any of them that are functional in the selected host cell may be used in conjunction with the NNT-1 gene. Therefore, the signal sequence may be homologous or heterologous to the NNT-1 polypeptide, and may be homologous or heterologous to the NNT-1 polypeptide. Additionally, the signal sequence may be chemically synthesized using methods set forth above. In most cases, secretion of the polypeptide from the host cell via the presence of a signal peptide will result in the removal of the amino terminal methionine from the polypeptide. Examples of secretory sequences useful for carrying out expression and secretion of NNT-1 polypeptides are selected from tPA leader sequences (see, e.g., Rickles et al., *J. Biol. Chem.* 263: 1563–1560 [1988]and Feng et al., *J. Biol. Chem.* 265: 2022–2027 [1990], EPO leader sequences and cardiotrophin leader sequences.

In many cases, transcription of the NNT-1 polypeptide is increased by the presence of one or more introns on the vector; this is particularly true where NNT-1 is produced in eukaryotic host cells, especially mammalian host cells. The introns used may be naturally occurring within the NNT-1 nucleic acid sequence, especially where the NNT-1 sequence used is a full length genomic sequence or a fragment thereof. Where the intron is not naturally occurring within the NNT-1 DNA sequence (as for most cDNAs), the intron(s) may be obtained from another source. The position of the intron with respect to the 5' flanking sequence and the NNT-1 coding sequence is important, as the intron must be transcribed to be effective. As such, where the NNT-1 nucleic acid sequence is a cDNA sequence, the preferred position for the intron is 3' to the transcription start site, and 5' to the polyA transcription termination sequence. Preferably for NNT-1 cDNAs, the intron will be located on one side or the other (i.e., 5' or 3') of the NNT-1 coding sequence such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vector such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector is to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with bacterial, insect, and/or mammalian host cells. Such vectors include, inter alia, pCRII (Invitrogen Company, San Diego, Calif.), pBSII (Stratagene Company, LaJolla, Calif.), and pETL (BlueBacII; Invitrogen).

After the vector has been constructed and an NNT-1 nucleic acid has been inserted into the proper site of the vector, the completed vector may be inserted into a suitable host cell for amplification and/or NNT-1 polypeptide expression.

Host cells may be prokaryotic host cells (such as *E. coli*) or eukaryotic host cells (such as a yeast cell, an insect cell, or a vertebrate cell). The host cell, when cultured under appropriate conditions, can synthesize NNT-1 protein which can subsequently be collected from the culture medium (if the host cell secretes it into the medium) or directly from the host cell producing it (if it is not secreted). After collection, the NNT-1 protein can be purified using methods such as molecular sieve chromatography, affinity chromatography, and the like.

Selection of the host cell will depend in part on whether the NNT-1 protein is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active protein is prepared by the cell. However, where the host cell does not synthesize biologically active NNT-1, the NNT-1 may be "folded" after synthesis using appropriate chemical conditions as discussed below.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas spp.*, other *Bacillus spp., Streptomyces spp.*, and the like may also be employed in this method.

Many strains of yeast cells known to those skilled in the art are also available as host cells for expression of the polypeptides of the present invention. Additionally, where desired, insect cells may be utilized as host cells in the method of the present invention (Miller et al., *Genetic Engineering* 8:277–298 [1986]).

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of NNT-1 polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the NNT-1 polypeptide has been designed to be secreted from the host cells, the majority of polypeptide may be found in the cell culture medium. Polypeptides prepared in this way will typically not possess an amino terminal methionine, as it is removed during secretion from the cell. If however, the NNT-1 polypeptide is not secreted from the host cells, it will be present in the cytoplasm (for eukaryotic, gram positive bacteria, and insect host cells) or in the periplasm (for gram negative bacteria host cells) and may have an amino terminal methionine.

For intracellular NNT-1 protein, the host cells are typically first disrupted mechanically or osmotically to release the cytoplasmic contents into a buffered solution. NNT-1 polypeptide can then be isolated from this solution.

Purification of NNT-1 polypeptide from solution can be accomplished using a variety of techniques. If the polypeptide has been synthesized such that it contains a tag such as Hexahistidine (NNT-1/hexaHis) or other small peptide at either its carboxyl or amino terminus, it may essentially be purified in a one-step process by passing the solution through an affinity column where the column matrix has a high affinity for the tag or for the polypeptide directly (i.e., a monoclonal antibody specifically recognizing NNT-1). For example, polyhistidine binds with great affinity and specificity to nickel, thus an affinity column of nickel (such as the Qiagen nickel columns) can be used for purification of NNT-1/polyHis. (See for example, Ausubele et al., eds., *Current Protocols in Molecular Biology*, Section 10.11.8, John Wiley & Sons, New York [1993]).

Where the NNT-1 polypeptide has no tag and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity. Preferred methods for purification include polyHistidine tagging and ion exchange chromatography in combination with preparative isoelectric focusing.

If it is anticipated that the NNT-1 polypeptide will be found primarily in the periplasmic space of the bacteria or the cytoplasm of eukaryotic cells, the contents of the periplasm or cytoplasm, including inclusion bodies (e.g., gram-negative bacteria) if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the NNT-1 polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The NNT-1 polypeptide in its now soluble form can then be analyzed using gel electrophoresis, immunoprecipitation or the like. If it is desired to isolate the NNT-1 polypeptide, isolation may be accomplished using standard methods such as those set forth below and in Marston et al. *Meth. Enz.,* 182:264–275 [1990]).

If NNT-1 polypeptide inclusion bodies are not formed to a significant degree in the periplasm of the host cell, the NNT-1 polypeptide will be found primarily in the supernatant after centrifugation of the cell homogenate, and the NNT-1 polypeptide can be isolated from the supernatant using methods such as those set forth below.

In those situations where it is preferable to partially or completely isolate the NNT-1 polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

B. Chemical Synthesis Methods

In addition to preparing and purifying NNT-1 polypeptide using recombinant DNA techniques, the NNT-1 polypeptides, fragments, and/or derivatives thereof may be prepared by chemical synthesis methods (such as solid phase peptide synthesis) using methods known in the art such as those set forth by Merrifield et al., (*J. Am. Chem. Soc.,* 85:2149 [1964]), Houghten et al. (*Proc Natl Acad. Sci. USA,* 82:5132 [1985]), and Stewart and Young (Solid Phase Peptide Synthesis, Pierce Chem Co, Rockford, IL [1984]). Such polypeptides may be synthesized with or without a methionine on the amino terminus. Chemically synthesized NNT-1 polypeptides or fragments may be oxidized using methods set forth in these references to form disulfide bridges. The NNT-1 polypeptides or fragments may be employed as biologically active or immunological substitutes for natural, purified NNT-1 polypeptides in therapeutic and immunological processes.

IV. Chemically Modified NNT-1 Derivatives

Chemically modified NNT-1 compositions (i.e., "derivatives") where the NNT-1 polypeptide is linked to a polymer ("NNT-1-polymers") are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of NNT-1-polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

For the acylation reactions, the polymer(s) selected should have a single reactive ester group. For reductive alkylation, the polymer(s) selected should have a single reactive aldehyde group. A preferred reactive aldehyde is polyethylene glycol propionaldehyde, which is water stable, or mono C1–C10 alkoxy or aryloxy derivatives thereof (see U.S. Pat. No. 5,252,714).

Pegylation of NNT-1 may be carried out by any of the pegylation reactions known in the art, as described for example in the following references: *Focus on Growth Factors* 3: 4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

Pegylation by acylation generally involves reacting an active ester derivative of polyethylene glycol (PEG) with an NNT-1 protein. Any known or subsequently discovered reactive PEG molecule may be used to carry out the pegylation of NNT-1. A preferred activated PEG ester is PEG esterified to N-hydroxysuccinimide ("NHS"). As used herein, "acylation" is contemplated to include without limitation the following types of linkages between NNT-1 and a water soluble polymer such as PEG: amide, carbamate, urethane, and the like, as described in *Bioconjugate Chem.* 5: 133–140 (1994). Reaction conditions may be selected from any of those known in the pegylation art or those subsequently developed, provided that conditions such as temperature, solvent, and pH that would inactivate the NNT-1 species to be modified are avoided.

Pegylation by acylation usually results in a poly-pegylated NNT-1 product, wherein the lysine ε-amino groups are pegylated via an acyl linking group. Preferably, the connecting linkage will be an amide. Also preferably, the resulting product will be at least about 95 percent mono, di- or tri-pegylated. However, some species with higher degrees of pegylation (up to the maximum number of lysine ε-amino acid groups of NNT-1 plus one α-amino group at the amino terminus of NNT-1) will normally be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Pegylation by alkylation generally involves reacting a terminal aldehyde derivative of PEG with a protein such as NNT-1 in the presence of a reducing agent. Regardless of the degree of pegylation, the PEG groups are preferably attached to the protein via a —$CH_2$—NH— group. With particular reference to the —$CH_2$— group, this type of linkage is referred to herein as an "alkyl" linkage.

Derivatization via reductive alkylation to produce a monopegylated product exploits the differential reactivity of different types of primary amino groups (lysine versus the N-terminal) available for derivatization in NNT-1. Typically, the reaction is performed at a pH (see below) which allows one to take advantage of the $pK_a$ differences between the ε-amino groups of the lysine residues and that of the α-amino group of the N-terminal residue of the protein. By such selective derivatization, attachment of a water soluble polymer that contains a reactive group such as an aldehyde, to a protein is controlled: the conjugation with the polymer occurs predominantly at the N-terminus of the protein without significant modification of other reactive groups such as the lysine side chain amino groups. The present invention provides for a substantially homogeneous preparation of NNT-1-monopolymer protein conjugate molecules (meaning NNT-1 protein to which a polymer molecule has been attached substantially only (i.e., at least about 95%) in a single location on the NNT-1 protein. More specifically, if polyethylene glycol is used, the present invention also provides for pegylated NNT-1 protein lacking possibly antigenic linking groups, and having the polyethylene glycol molecule directly coupled to the NNT-1 protein.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy-or aryloxy-polyethylene glycol.

In general, chemical derivatization may be performed under any suitable conditions used to react a biologically active substance with an activated polymer molecule. Methods for preparing pegylated NNT-1 will generally comprise the steps of (a) reacting an NNT-1 polypeptide with polyethylene glycol (such as a reactive ester or aldehyde derivative of PEG) under conditions whereby NNT-1 becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

Reductive alkylation to produce a substantially homogeneous population of mono-polymer/NNT-1 protein conjugate molecule will generally comprise the steps of: (a) reacting an NNT-1 protein with a reactive PEG molecule under reductive alkylation conditions, at a pH suitable to permit selective modification of the α-amino group at the amino terminus of said NNT-1 protein; and (b) obtaining the reaction product(s).

For a substantially homogeneous population of mono-polymer/NNT-1 protein conjugate molecules, the reductive alkylation reaction conditions are those which permit the selective attachment of the water soluble polymer moiety to the N-terminus of NNT-1. Such reaction conditions generally provide for $pK_a$ differences between the lysine amino groups and the α-amino group at the N-terminus (the $pK_a$ being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal α-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–5, preferably 4–5.

Another important consideration is the molecular weight of the polymer. In general, the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa (the term "about" indicating ±1 kDa). The preferred average molecular weight is about 5 kDa to about 50 kDa, particularly preferably about 12 kDa to about 25 kDa. The ratio of water-soluble polymer to NNT-1 protein will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any NNT-1 protein having an α-amino group at the amino terminus, and provide for a substantially homogenous preparation of monopolymer/NNT-1 protein conjugate. The term "monopolymer/NNT-1 protein conjugate" is used here to mean a composition comprised of a single polymer molecule attached to an NNT-1 protein molecule. The monopolymer/ NNT-1 protein conjugate preferably will have a polymer molecule located at the N-terminus, but not on lysine amino side groups. The preparation will preferably be greater than 90% monopolymer/NNT-1 protein conjugate, and more preferably greater than 95% monopolymer NNT-1 protein conjugate, with the remainder of observable molecules being unreacted (i.e., protein lacking the polymer moiety). The examples below provide for a preparation which is at least about 90% monopolymer/protein conjugate, and about 10% unreacted protein. The monopolymer/protein conjugate has biological activity.

For the present reductive alkylation, the reducing agent should be stable in aqueous solution and preferably be able to reduce only the Schiff base formed in the initial process of reductive alkylation. Preferred reducing agents may be selected from the group consisting of sodium borohydride, sodium cyanoborohydride, dimethylamine borane, trimethylamine borane and pyridine borane. A particularly preferred reducing agent is sodium cyanoborohydride.

Other reaction parameters, such as solvent, reaction times, temperatures, etc., and means of purification of products, can be determined based on the published information relating to derivatization of proteins with water soluble polymers.

A mixture of polymer-NNT-1 protein conjugate molecules may be prepared by acylation and/or alkylation methods, as described above, and one may select the proportion of monopolymer/protein conjugate to include in the mixture. Thus, where desired, a mixture of various protein with various numbers of polymer molecules attached (i.e., di-, tri-, tetra.-, etc.) may be prepared and combined with the monopolymer/NNT-1 protein conjugate material prepared using the present methods.

Generally, conditions which may be alleviated or modulated by administration of the present polymer/NNT-1 include those described herein for NNT-1 molecules in general. However, the polymer/NNT-1 molecules disclosed herein may have additional activities, enhanced or reduced activities, or other characteristics, as compared to the non-derivatized molecules.

V. Combinations

The NNT-1 polypeptides and fragments thereof, whether or not chemically modified, may be employed alone, or in combination with other pharmaceutical compositions such as, for example, neurotrophic factors, cytokines, interferons, interleukins, growth factors, antibiotics, anti-inflammatories, neurotransmitter receptor agonists or antagonists and/or antibodies, in the treatment of neurological system disorders.

VI. Antibodies

The NNT-1 polypeptides, fragments, and/or derivatives thereof may be used to prepare antibodies generated by standard methods. Thus, antibodies that react with the NNT-1 polypeptides, as well as reactive fragments of such antibodies, are also contemplated as within the scope of the present invention. The antibodies may be polyclonal, monoclonal, recombinant, chimeric, single-chain and/or bispecific. Typically, the antibody or fragment thereof will be "humanized", i.e., prepared so as to prevent or minimize an immune reaction to the antibody when administered to a patient. The antibody fragment may be any fragment that is reactive with the NNT-1 of the present invention, such as, $F_{ab}$, $F_{ab'}$, etc. Also provided by this invention are the hybridomas generated by presenting NNT-1 or a fragment thereof as an antigen to a selected mammal, followed by fusing cells (e.g., spleen cells) of the mammal with certain cancer cells to create immortalized cell lines by known techniques. The methods employed to generate such cell lines and antibodies directed against all or portions of a human NNT-1 polypeptide of the present invention are also encompassed by this invention.

The antibodies may be used therapeutically, such as to inhibit binding of NNT-1 to its receptor. The antibodies may further be used for in vivo and in vitro diagnostic purposes, such as in labeled form to detect the presence of the NNT-1 in a body fluid.

VII. Therapeutic Compositions and Administration Thereof

As used herein, the terms "effective amount" and "therapeutically effective amount" refer to the amount of NNT-1 necessary to support one or more biological activities of NNT-1 as set forth above.

Therapeutic compositions for treating various neurological disorders or diseases are within the scope of the present invention. Such compositions may comprise a therapeutically effective amount of an NNT-1 polypeptide or fragment thereof (either of which may be chemically modified) in admixture with a pharmaceutically acceptable carrier. The carrier material may be water for injection, preferably supplemented with other materials common in solutions for administration to mammals. Typically, an NNT-1 therapeutic compound will be administered in the form of a composition comprising purified NNT-1 polypeptide or fragment (which may be chemically modified) in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. An exemplary composition comprises citrate buffer of about pH 4.0–4.5, which may further include NaCl.

The NNT-1 compositions can be systemically administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of NNT-1 compositions useful for practicing the present invention may be prepared for storage by mixing the selected composition having the desired degree of purity with optional physiologically acceptable carriers, excipients, or stabilizers (*Remington's Pharmaceutical Sciences*, 18th edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The NNT-1 composition to be used for in vivo administration must be sterile. This is readily accomplished by filtration through sterile filtration membranes. Where the NNT-1 composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device. Alternatively or additionally, NNT-1 may be administered locally via implantation into the affected area of a membrane, sponge, or other appropriate material on to which NNT-1 polypeptide has been absorbed.

Where an implantation device is used, the device may be implanted into any suitable tissue or organ, such as, for example, into a cerebral ventricle or into brain parenchyma, and delivery of NNT-1 may be directly through the device via bolus or continuous administration, or via a catheter using continuous infusion.

NNT-1 polypeptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamine (Sidman et al, *Biopolymers*, 22:547–556 [1983]), poly (2-hydroxyethyl-methacrylate) (Langer et al., *J. Biomed. Mater. Res.*, 15: 167–277 [1981] and Langer, *Chem. Tech.*, 12: 98–105 [1982]), ethylene vinyl acetate (Langer et al., supra) or poly-D(-)-3-hydroxybutyric acid (EP 133,988). Sustained-release compositions also may include liposomes, which can be prepared by any of several methods known in the art (e.g., DE 3,218,121; Epstein et al., *Proc. Natl. Acad. Sci. USA*, 82: 3688–3692 [1985]; Hwang et al., *Proc. Natl. Acad. Sci. USA*, 77: 4030–4034 [1980]; EP 52,322; EP 36,676; EP 88,046; EP 143,949).

In some cases, it may be desirable to use NNT-1 compositions in an ex vivo manner, i.e., to treat cells or tissues that have been removed from the patient and are then subsequently implanted back into the patient.

In other cases, NNT-1 may be delivered through implanting into patients certain cells that have been genetically engineered to express and secrete NNT-1 polypeptide. Such cells may be animal or human cells, and may be derived from the patient's own tissue or from another source, either human or non-human. Optionally, the cells may be immortalized. The cells may be implanted into the brain, adrenal gland or into other suitable body tissues or organs of the patient.

In certain situations, it may be desirable to use gene therapy methods for administration of NNT-1 to patients suffering from certain neurological disorders. In these situations, genomic DNA, cDNA, and/or synthetic DNA encoding NNT-1 or a fragment or variant thereof may be operably linked to a constitutive or inducible promoter that is active in the tissue into which the composition will be injected. This NNT-1 DNA construct, either inserted into a vector, or alone without a vector, can be injected directly into brain or other tissue, either neuronal or non-neuronal.

Alternatively, an NNT-1 DNA construct may be directly injected into muscle tissue where it can be taken up into the cells and expressed in the cells, provided that the NNT-1 DNA is operably linked to a promoter that is active in muscle tissue such as cytomegalovirus (CMV) promoter, Rous sarcoma virus (RSV) promoter, or muscle creatine kinase promoter. Typically, the DNA construct may include (in addition to the NNT-1 DNA and a promoter), vector sequence obtained from vectors such as adenovirus vector, adeno-associated virus vector, a retroviral vector, and/or a herpes virus vector. The vector/DNA construct may be admixed with a pharmaceutically acceptable carrier(s) for injection.

An effective amount of the NNT-1 composition(s) to be employed therapeutically will depend, for example, upon the therapeutic objectives such as the indication for which NNT-1 is being used, the route of administration, and the condition of the patient. Accordingly, it will be necessary for the therapist to titer the dosage and modify the route of administration as required to obtain the optimal therapeutic effect. A typical daily dosage may range from about 0.1 µg/kg to up to 10 mg/kg or more, depending on the factors mentioned above. Typically, a clinician will administer the NNT-1 composition until a dosage is reached that achieves the desired effect. The NNT-1 composition may therefore be administered as a single dose, or as two or more doses (which may or may not contain the same amount of NNT-1) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

VIII. Conditions to be Treated with NNT-1

The NNT-1 proteins, fragments and/or derivatives thereof may be utilized to treat diseases and disorders of the central or peripheral nervous system which may be associated with alterations in the pattern of NNT-1 expression or which may benefit from exposure to NNT-1 or anti-NNT-1 antibodies.

NNT-1 protein and/or fragments or derivatives thereof, may be used to treat patients in whom various cells of the central, autonomic, or peripheral nervous system have degenerated and/or have been damaged by congenital disease, trauma, mechanical damage, surgery, stroke, ischemia, infection, metabolic disease, nutritional deficiency, malignancy, and/or toxic agents. More specifically, NNT-1 protein levels may be modulated (up or down regulated) for such indications as Alzheimer's, Parkinson's, amyotrophic lateral sclerosis, Charcot-Marie-Tooth syndrome, Huntington's disease, peripheral neuropathy induced by diabetes or other metabolic disorder, and/or dystrophies or degeneration of the neural retina such as retinitis pigmentosa, drug-induced retinopathies, stationary forms of night blindness, progressive cone-rod degeneration, and the like. Since NNT-1 is also expressed in immune system cells (see Example V below), it may also be useful to treat diseases caused by immune disorders. Further, since NNT-1 is also expressed in hematopoietic cells (see Example V below), it may also be useful to treat diseases caused by disorders of the hematopoietic system.

IX. Assays to Screen for Inhibitors of NNT-1

In some situations, it may be desirable to inhibit or significantly decrease the level of NNT-1 activity. Compounds that inhibit NNT-1 activity could be administered either in an ex vivo manner, or in an in vivo manner by local or iv injection, or by oral delivery, implantation device, or the like. The assays described below provide examples of methods useful for identifying compounds that could inhibit NNT-1 activity.

For ease of reading, the following definition is used herein for describing the assays:

"Test molecule(s)" refers to the molecule(s) that is under evaluation as an inhibitor of NNT-1, typically by virtue of its potential ability to block the interaction of NNT-1 with its receptor.

The NNT-1 receptor may be isolated, for example, by expression cloning using labeled e.g., iodinated) NNT-1.

Several types of in vitro assays using purified protein may be conducted to identify those compounds that disrupt NNT-1 activity. Such disruption may be accomplished by a compound that typically inhibits the interaction of NNT-1 with its receptor.

In one assay, purified NNT-1 protein or a fragment thereof (prepared for example using methods described above) can be immobilized by attachment to the bottom of the wells of a microtiter plate. Radiolabeled NNT-1 receptor, as well as the test molecule(s) can then be added either one at a time or simultaneously to the wells. After incubation, the wells can be washed and counted using a scintillation counter for radioactivity to determine the degree of NNT-1/receptor binding in the presence of the test molecule. Typically, the molecule will be tested over a range of concentrations, and a series of control "wells" lacking one or more elements of the test assays can be used for accuracy in evaluating the results. A variation of this assay involves attaching the receptor to the wells, and adding radiolabeled NNT-1 along with the test molecule to the wells. After incubation and washing, the wells can be counted for radioactivity.

Several means including radiolabelling are available to "mark" NNT-1. For example, NNT-1 protein can be radiolabelled using 125-I or 35-S. Alternatively, a fusion protein of NNT-1 wherein the DNA encoding NNT-1 is fused to the coding sequence of a peptide such as the c-myc epitope. NNT-1-myc fusion protein can readily be detected with commercially available antibodies directed against myc.

An alternative to microtiter plate type of binding assays comprises immobilizing either NNT-1 or its receptor on agarose beads, acrylic beads or other types of such inert substrates. The inert substrate containing the NNT-1 or its receptor can be placed in a solution containing the test molecule along with the complementary component (either receptor or NNT-1 protein) which has been radiolabeled or fluorescently labeled; after incubation, the inert substrate can be precipitated by centrifugation, and the amount of binding between NNT-1 and receptor can be assessed using the methods described above. Alternatively, the insert substrate complex can be immobilized in a column and the test molecule and complementary component passed over the column. Formation of the NNT-1/receptor complex can then be assessed using any of the techniques set forth above, i.e., radiolabeling, antibody binding, or the like.

Another type of in vitro assay that is useful for identifying a molecule to inhibit NNT-1 activity is the Biacore assay system (Pharmacia, Piscataway, N.J.) using a surface plasmon resonance detector system and following the manufacturer's protocol. This assay essentially involves covalent binding of either NNT-1 or its receptor to a dextran-coated sensor chip which is located in a detector. The test molecule and the complementary component can then be injected into the chamber containing the sensor chip either simultaneously or sequentially, and the amount of binding of NNT-1/receptor can be assessed based on the change in molecular mass which is physically associated with the dextran-coated side of the of the sensor chip; the change in molecular mass can be measured by the detector system.

In some cases, it may be desirable to evaluate two or more test molecules together for use in decreasing or inhibiting NNT-1 activity. In these cases, the assays set forth above can be readily modified by adding such additional test molecule (s) either simultaneously with, or subsequently to, the first test molecule. The remainder of steps in the assay can be as set forth above.

X. Transgenic Mammals

Also included within the scope of the present invention are non-human mammals such as mice, rats, rabbits, goats, or sheep in which the gene (or genes) encoding the human equivalent of NNT-1 has been disrupted ("knocked out") such that the level of expression of this gene is significantly decreased or completely abolished. Such mammals may be prepared using techniques and methods such as those described in U.S. Pat. No. 5,557,032. The present invention further includes non-human mammals such as mice, rats, rabbits, goats, or sheep in which the gene (or genes) encoding the NNT-1 (either the native form of NNT-1 for the mammal or a heterologous NNT-1 gene) is over expressed by the mammal, thereby creating a "transgenic" mammal. Such transgenic mammals may be prepared using well known methods such as those described in U.S. Pat. No. 5,489,743 and PCT patent application no. WO94/28122, published 8 Dec.1994.

The following examples are intended for illustration purposes only, and should not be construed as limiting the scope of the invention in any way.

EXAMPLES

Standard methods for library preparation, DNA cloning, and protein expression are set forth in Sambrook et al. (*Molecular Cloning: A Laboratory Manual*, Cold Spring Harbor Laboratory Press, Cold Spring Harbor, N.Y. [1989]) and in Ausubel et al, eds. (*Current Protocols in Molecular Biology*, Wiley, New York, N.Y. [1995]).

Example I: Cloning of cDNA and Genomic Clone for NNT-1

A. Construction of cDNA library

Human T-cell lymphoma cells, Jurkat cells, were grown at 37° C. under 5% $CO_2$ in a RPMI 400 media containing 10% fetal bovine serum. The media was buffered with 10 mM HEPES, pH 7.5. After 8 passages the cells were divided into two groups. One group was grown to confluency ($2\times10^7$ cells/flask), the RNA harvested from these cells served as the "driver" RNA. The other group was the "tester" group and were activated with the following treatment.

The cells were activated for 8 hours by adding the superantigens Streptococci enterotoxin B and F(TSST) 80 ng/ml; the PKC activator, PMA 50 ng/ml; calcium ionophore A21832 125 ng/ml. The protein translation inhibitor cycloheximide was also added at a concentration of 1 mg/ml. RNA was harvested from the different groups of cells at different time points.

1. Total RNA preparation:

The cells were pelleted by centrifugation at 300×g for 5 min and washed with PBS (phosphate buffered saline), and resuspended in Ultraspec II (Biotex, Inc., Tex.), at a concentration of $5 \times 10^6$ cells/ml of Ultraspec II. The cells were then lysed by four passages through a 21-gauge syringe. The homogenate was incubated on ice for 15 min, 0.2 volumes of chloroform was then added, mixed well, and reincubated on ice for a further 10 min, centrifuged at 12000×g for 30 min in 30 ml corex tubes. Post-centrifugation and supernatant was saved and the residue discarded. 0.05 volumes of the RNA binding resin sold by Biotex as part of the isolation kit was added after the addition of 0.5 volumes of isopropanol. After pelleting the resin by centrifugation (300×g for 5 min), the resin was washed twice with 75% RNase-free ethanol, and air dried at 50° C. for 10 min. Total RNA was then eluted from the resin by resuspending the resin in 1 volume RNase-free water, vortexing vigorously for 1 min, then centrifugated at 13000×g for 1 min. The total RNA was then transferred to a new Eppendorf tube and the resin pellet discarded.

2. Poly(A)+ RNA isolation:

Qiagen's Oligotex mRNA isolation system was used as described by the manufacturer; the procedure was repeated twice to obtain pure poly(A)+ RNA. This is especially important for a random primed library to minimize the number of copies of ribosomal RNA in the cDNA. The mRNA integrity was then determined by both spectroscopy and formamide denaturing gel electrophoresis.

The first strand cDNA was synthesized by following the BRL cDNA synthesis protocol. To remove residual mRNA from the target cDNA, the first-strand cDNA reaction was phenol/chloroform extracted and precipitated with 2M ammonium acetate and 3 volumes of ethanol. The cDNA/mRNA hybrids were then resuspended in 0.3M NaOH in the presence of 2 mM EDTA and incubated at 68° C. for 15 min. The hydrolysis reaction was neutralized with about 1.5M excess of pure Tris HCl . The cDNA was then phenol/chloroform extracted and reprecipitated with 2M ammonium acetate and 3 volumes of ethanol, rinsed with 75% ethanol, and resuspended in 7 ml of sterile water. The single strand cDNA was tailed by following the protocol of Boehringer Mannheim tailing kit.

3. Driver mRNA preparation and photo-biotinylation:

Poly(A) RNA was isolated as described above. Approximately 20 mg was then photobiotinylated twice with 20 mg photobiotin acetate (Sigma), and reconstituted at a concentration of 1 mg/ml in RNase-free water. Excess photobiotin was removed with water saturated isobutanol, and ethanol precipitated and resuspended in 30 ml DEPC-treated water.

4. Subtractive hybridization reaction:

The photobiotinylated driver mRNA was coprecipitated with the tester cDNA and resuspended in 2 ml RNase-free water. To allow the nucleic acids to go into solution, the preparation was left at room temperature for a few hours with intermittent gentle stirring followed by another 20 hours incubation at 68° C. Photobiotinylated driver was dissolved to a final concentration of 2 mg/ml. In general, a concentration of driver RNA of at least 1 mg/ml should be used.

5. Post-hybridization hybrid removal:

After the hybridization, streptavidin was added to a final concentration of 0.2 mg/ml and incubated at room temperature for 10 min. The streptavidin was then removed with a phenol/chloroform extraction. After the extraction, the cDNA was precipitated with ethanol. A pair of primers: AGCGCTACGGTCGACCCG GCG TTT TTT TTT TTT TTT TTT TTT (ACG)X (SEQ ID NO:15) (Sal I T21 anchored primer) and GGA AGG AAA AAA GCG GCC GCT ACA (SEQ ID NO:16) (Not I-N9 primer) were used in PCR to amplify cDNA. The expend PCR kit was used. Fifteen cycles were used to generate enough material for gel fractionation approach to allow for an equal size representation in the library. To allow for the annealing of the first primer, the annealing temperature of the initial five cycles of the PCR were performed at 35° C. for 1 min. The cDNA representing different size fractions were fractionated on a gel. SalI adapters were added to the duplex cDNA, which was then digested with NotI and cloned into pSport vector.

B. Isolation of cDNA Clone

The library was screened by EST analysis. Individual clones from this library were randomly picked and sequenced on an Applied Biosystems 373A automated DNA sequencer using vector primer and Taq dye-terminator reactions (Applied Biosystems). The resulting nucleotide sequence obtained from the randomly picked clone NNT-1 was translated, then compared to the existing database of known protein sequences using a modified version of the FASTA program.

One clone (khjl-00008-f2) has about 21% homology at translated amino acid sequence level with CNTF. The entire insert of the cDNA clone was sequenced and found to encode a full-length clone, i.e., it contains Met at the 5' end and one stop codon upstream of Met and another stop codon at the 3' end.

The sequence of this full-length cDNA is shown in FIG. 1. The predicted amino acid sequence of the protein is shown in FIG. 3. The putative signal peptide spanned from amino acid −27 (Met) to amino acid −1 (Ala).

C. Isolation of the Genomic Clone

The genomic DNA of NNT-1 was obtained from a human genomic P1 library (Genome Systems Inc., St. Louis, Mo.; catalog no. P1-2535). The library was screened using the NNT-1 cDNA as a probe. The cDNA was radiolabeled using the Amersham Rediprime kit (Amersham, Arlington Heights, Ill.; catalog no. RPN-1633) and the hybridization and prehybridization solution was: 50 percent formamide, 5×SSC, 5×Denhardt's, 0.05 percent sodium pyrophosphate, 0.1 percent SDS, and 100 mg/ml salmon sperm DNA. Prehybridization was for about 1 hour, and hybridization was for about 16 hours at 42° C.

After hybridization, the filters were washed in 0.2×SSC and 0.1 percent SDS at 42° C. for about 30 minutes, and then exposed to film. Two positive clones were identified, and the plasmids containing these clones were purified according to Genome Systems Inc. protocols. The plasmid DNA was then sequenced directly.

The genomic sequence encoding NNT-1 is shown in FIG. 2 (SEQ ID NO:3). The gene consists of 3 exons and 2 introns. The coding regions are presented in uppercase, while the noncoding regions, including 5' untranslated region, introns and 3' untranslated region are presented in lower case.

Example II: Preparation of Recombinant Mammalian Protein of NNT-1

An expression vector containing human NNT-1 cDNA and flag-tag peptide was constructed by PCR amplification of the fusion gene. A sense primer with Hind III site at the 5' end:
(5'-AGCAAGCTTCACCATGGACCTCCGAGCAGGGG-ACTC-3')
(SEQ ID NO: 6)
which encodes amino acid −27 (Met) to amino acid −21 (Asp) and an anti-sense primer with NotI site at the 5' end which encode for flag-tag peptide and the last 8 amino acids of the 3' end (5'AGCGGGGCCGCACTACTTGRCATCGTCGRCGTCC-
TTGTACTCGAAGCCATGAG CCCCCAGGTGCAG-
3') (SEQ ID NO: 7)
were used in PCR to amplify a fusion gene. The fusion gene was ligated into the P CEP4 vector (Invitrogen Inc., San Diego, Calif.). The expression vector was transfected into EBNA-1 293 cells with lipofectin (BRL, Gaithersburg, Md.) using the manufacturer's recommended method. Forty-eight hours after transfection, both 293 cells and the conditioned medium were harvested and analyzed in Western blot by using the anti-flag-tag antibody (Eastman Kodak Co., New Haven Conn.). The majority of recombinant protein was found in the 293 cell lysate. Therefore, anti-flag antibody gel (Eastman Kodak Co., New Haven, Conn.) was used to purify the protein from the 293 cell lysate. A 28–30 kd protein was purified following the manufacturer's protocol. This recombinant protein was used in the biological function analysis (for motor neuron and sympathetic neuron survival assay). The N-terminal amino acid of the protein was determined to be Leu (amino acid 1) indicating that the potential signal peptide was cleaved (amino acid −27 to amino acid −1).

Example III: Preparation of Recombinant E coli NNT-1 Protein

A cDNA clone of NNT-1 encoding amino acids Leu (1) to Phe (198) of SEQ ID NO: 2 was inserted into the vector pAMG21 which is a derivative of pCFM 1656 (ATCC accession number 69576) and contains appropriate restriction sites for insertion of genes downstream from the lux PR promoter (see U.S. Pat. No. 5,169,318 for a description of the lux expression system). The host cell used was E. coli K12, strain CGSC 6159 (Yale University genetic stock, New Haven, Conn.). The host cells were transformed with the vector using standard transformation procedures, and were then incubated in 2 XYT medium containing about 50 ul/ml kanamycin at 30° C. Induction of NNT-1 gene product was commenced by adding the autoinducer N-(3-oxohexanoyl)-DL-homoserine lactone to the culture medium to a final concentration of about 30 ng/ml, and the cultures were incubated at either 30° C. or 37° C. for about 6 hours after which time the cells were examined by microscopy for inclusion bodies.

The majority of NNT-1 protein was found to be located in the inclusion bodies. Therefore, a cell paste was prepared by pelleting the cells. The inclusion bodies were solubilized at low pH and the protein was purified by sequential precipitation. The protein was dialyzed before loading a sample on to SDS-PAGE to assess purity. Coomassie staining of the gel indicated that the protein was at least 95 percent pure.

Example IV: Biological function of NNT-1
A. Chick Motor Neuron Assay

Motor neurons (MN) enriched culture from lumbar spinal cord were prepared from embryonic day E5.5 chicks. MN neurons were enriched by using a 6.8% metrizamide gradient. In brief, lumbar spinal cords were dissected, freed of meninges and DRG. Spinal cords were incubated in papain containing L15 medium (Gibco/BRL, Grand Island, N.Y.) for 20 minutes at 37° C. (Worthington Biochemical Corp. Freehold, N.J.). Enzymatically softened spinal cord fragments were dissociated into single cells by pipetting. The cell suspension was then layered onto a 6.8% metrizamide (Serva, Feinbiochemicala, Germany) cushion, and the tube was centrifuged at 500 g for 20 minutes. The interface between metrizamide cushion and cell suspension was collected and diluted into culture medium. The fraction was then gently layered onto a 4% BSA cushion and centrifuged at 280 g for 10 minutes. The pellet was resuspended in culture medium containing L15 medium with 10% fetal bovine serum supplemented with 3.6 mg/ml glucose, 5 ng/ml sodium selenite, 6.25 ng/ml progesterone, 0.1 mg/ml conalbumin, 16 mg/ml putrescine, and 5 mg/ml insulin. 10,000 cells/well were seeded into 96 well tissue culture plates. Serial dilutions of the neurotrophic factor (NNT-1 or CNTF) were added to the culture and incubated for 3 days. At day 3, MTT was added into the culture for 4.5 hours. The formazan product was solubilized, and the plates were read at 570 wavelength with a 650 subtraction for visible interference. The optical density (OD) reading is proportional to the number of surviving neurons in culture. The absorbance at 570 nm (increasing neuron survival) in triplicate wells is plotted as a function of final concentration of NNT-1 or CNTF.

Results of the analysis are presented in FIG. 7. The absorbance at 570 nm is expressed as 1000 fold of the actual reading. The results showed that NNT-1 can support chick motor meuron growth. Its maximal activity reaches about 90% that of CNTF.

B. Chick Sympathetic Neuron Assay

Cultures of primary chick embryo sympathetic chain ganglia were prepared. Briefly, sympathetic ganglia were removed from fertile, pathogen-free chicken eggs that had been incubated for 9 days at 37.6° C. in a humidified atmosphere. The ganglia were chemically dissociated by exposure first to Hanks' Balanced Salt Solution without divalent cations, containing 10 mM HEPES buffer pH 7.2 for 10 min at 37° C., and then by exposure to a solution of 0.125% bactotrypsin 1:250 (Difco, Detroit, Mich.) in Hanks' Balanced Salt Solution modified as above for 12 min at 37° C. Trypsinization was stopped by addition of fetal calf serum to a final concentration of 10%.

After this treatment, ganglia were transferred to a solution consisting of Dulbecco's high glucose Modified Eagle's Medium with bicarbonate contain 10% fetal calf serum and 10 mM HEPES, pH 7.2 and were mechanically dissociated by trituration approximately 14 times through a 20-gauge, 1" double-hubbed stainless steel needle.

The dissociated ganglia were then plated in culture medium (Dulbecco's Modified Eagle Medium supplemented with 10% fetal calf serum, 4 mM glutamine, 60 mg/L penicillin-G, 25 mM HEPES, pH 7.2) in 100 mm diameter tissue culture dishes (approximately 40 dissociated ganglia per dish) for two to three hours. This preplating was done in order to separate the nonneuronal cells, which adhere to the dish, from the nerve cells, which do not adhere. After preplating, the nonadherent nerve cells were collected by centrifugation, resuspended in culture medium, and plated in 50 ml per well onto half area 96-well microtiter tissue culture plates at a density of 2500 nerve cells per well. The microtiter wells had been previously exposed to a 1 mg/ml solution of poly-L-ornithine in 10 mM sodium borate, pH 8.4 overnight at 4° C., washed in sterile purified water ad air-dried.

Final concentrations of neurotrophic factors to which the cells were exposed are as follows: 1) for the CNTF standard, nine-point serial dilution curves ranged from 100 ng/ml to 6 pg/ml; 2) for the NNT-1 protein, nine-point serial dilutions curves ranged from 100 ng/ml to 0.12 pg/ml. Twenty-five ml of a serial dilution of the sample to be assayed for neurotrophic activity was added to each well and the dishes were incubated for 38–46 hours at 37° C. in a humidified atmosphere containing 7.5% $CO_2$. Then 18 ml per well of a 1.5 mg/ml solution of the tetrazolium dye MTT in Dulbecco's high glucose Modified Eagle Medium with bicarbonate contain 10 mM HEPES, pH 7.2 was added, and the cultures were placed in the 37° C. incubator for 4.5 hours. Then 75 ml of a solution of 50% N,N-dimethyl formamide containing 20% sodium dodecyl sulfate, pH 4.7 was added to dissolve the crystalline formazan product and the plates were incubated in the 37° C. incubator for a minimum of 12 hours. The absorbance at 579 nm was determined relative to a 650 nm reference for each well using an automatic microtiter plate reader. The resulting absorbance is proportional to the number of living cells in each well, defined as those nerve cells capable of reducing the dye.

Figure 8:
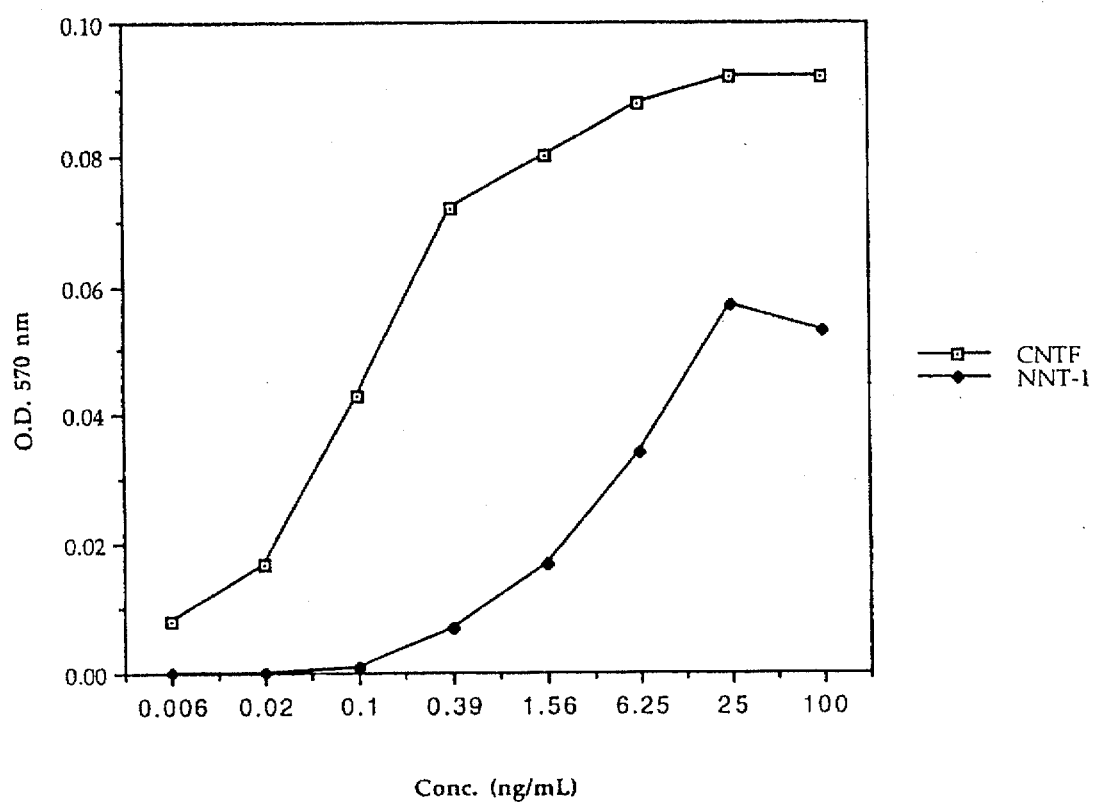
FIG. 8 depicts a graph of the results of a chick sympathetic neuron activity assay for human NNT-1 compared to human CNTF.

Results of the analysis are presented in FIG. 8. The results demonstrate that NNT-1 supports chick sympathetic neuron growth.

Example V: Northern Blot Analysis of Tissue Distribution

Northern blots of human tissues were purchased from Clontech (Palo Alto, Calif.). The Northern blots were probed with a human NNT-1 cDNA probe. Two cDNA fragments spanning the 5' and 3' coding region of NNT-1 were labeled and used as a probe to analyze the tissue expression of the NNT-1 gene. The result showed that NNT-1 was expressed as a 2.2 kb transcript in the tissues of spleen, lymph node and peripheral blood lymphocytes, bone marrow and fetal liver, kidney, lung, colorectal adenocarcinoma cells SW480, Hela cell S3, lung carcinoma A 549, chronic myelogenous leukemia K-562 cells, Burkitt's lymphoma Raji cells. The tissue distribution of the gene suggests that the gene may be also involved in development of the immune system or of hematopoietic cells.

Example VI: Chromosome localization of the NNT-1 gene

Chromosome localization of the gene was performed by FISH. A 14 kb genomic fragment was biotinylated with dATP using BRL BioNick labeling kit. (15° C. 1 hour). The procedure for FISH was performed according to Heng et al., 1992 (Proc Nat Acad Sci USA 89:9509–9513). The result showed that the gene is located on chromosome 11 q13 which is close to the human CNTF gene locus (chromosome 11 q12).

Example VII: Isolation of mouse cDNA clone

A mouse partial cDNA clone was isolated by PCR amplification from the mouse 11 day-embryo cDNA (Clontech, Palo Alto, Calif.) using the human specific primer. The full-length cDNA clone was further obtained by 5' RACE and 3' RACE. The mouse cDNA nucleotide sequence and amino acid sequence are shown in FIGS. 4 and 5, respectively. The mouse protein shares 96% identity with the human protein, indicating that the protein is highly conserved throughout evolution. Like the human protein, the mouse protein also contains a potential N-linked glycosylation site at amino acid 2 (Asn).

Example VIII: Comparison of NNT-1 with other members of the family

The amino acid sequence of NNT-1 suggests that the protein belongs to the family of CNTF which includes, CNTF (SEQ ID NO:12), which includes IL-11 (SEQ ID NO:8), IL-6 (SEQ ID NO:9), cardiotrophin (SEQ ID NO:11), oncostatin (SEQ ID NO:13) and granulocyte colony-stimulating factor (G-CSF) (SEQ ID NO:10). We compared the amino acid sequence of NNT-1 with all of the members of the family by the computer program PILEUP and the results are shown in FIG. 6. As with all the other members of this family, the secondary structure of the NNT-1 protein was predicted to contain four anti-parallel alpha-helices.

Deposit of DNA

E. coli cells DH10B containing the vector P1 encoding human genomic DNA for NNT-1 (NNT-g-PI) and E. coli cells DH10B containing the vector PSPORT encoding human cDNA for NNT-1 have been deposited with the ATCC (American Type Culture Collection, 12301 Parklawn Drive, Rockville, Md., USA) on Jan. 21, 1997 and assigned accession numbers 98294 and 98295, repectively.

---

I claim:

1. An NNT-1 polypeptide, which has a biological activity of stimulating growth of motor or sympathetic neurons, selected from the group consisting of:
   (a) the polypeptide of SEQ ID NO:2;
   (b) the polypeptide that is amino acids 1–198 of SEQ ID NO:2;
   (c) the polypeptide that is at least 70 percent identical to the polypeptide of (a) or (b); and
   (d) a fragment of any of (a)–(c), which has said biological activity.

2. An NNT-1 polypeptide, which has a biological activity of stimulating growth of motor or sympathetic neurons, selected from the group consisting of:
   (a') the polypeptide of SEQ ID NO:5;
   (b') the polypeptide that is amino acids 1–198 of SEQ ID NO:5;
   (c') the polypeptide that is at least 70 percent identical to the polypeptide of (a') or (b'); and
   (d') a fragment of any of (a')–(c'), which has said biological activity.

3. An NNT-1 polypeptide, which has a biological activity of stimulating growth of motor or sympathetic neurons, that is the polypeptide of SEQ ID NO:2 or a fragment of said polypeptide which has said biological activity.

4. An NNT-1 polypeptide, which has a biological activity of stimulating growth of motor or sympathetic neurons, that is the polypeptide of SEQ ID NO:5 or a fragment of said polypeptide which has said biological activity.

5. The NNT-1 polypeptide of claim 3 or 4 that does not possess an amino terminal methionine.

6. The NNT-1 polypeptide of claim 3 or 4 that additionally possesses an amino terminal methionine.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
      ( A ) LENGTH: 797 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 90..764

( i x ) FEATURE:
      ( A ) NAME/KEY: mat_peptide
      ( B ) LOCATION: 171..764

( i x ) FEATURE:
      ( A ) NAME/KEY: sig_peptide ( B ) LOCATION: 90..170

( x i ) SEQUENCE DESCRIPTION: SEQ ID NO:1:

```
ATTAAAGCTT CGCCGGAGCC GCGGCTCGCC CTCCCACTCC GCCAGCCTCC GGGAGAGGAG        60

CCGCACCCGG CCGGCCCAGC CCCAGCCCC ATG GAC CTC CGA GCA GGG GAC TCG         113
                                Met Asp Leu Arg Ala Gly Asp Ser
                                -27     -25                     -20

TGG GGG ATG TTA GCG TGC CTG TGC ACG GTG CTC TGG CAC CTC CCT GCA         161
Trp Gly Met Leu Ala Cys Leu Cys Thr Val Leu Trp His Leu Pro Ala
            -15                     -10                         -5

GTG CCA GCT CTC AAT CGC ACA GGG GAC CCA GGG CCT GGC CCC TCC ATC         209
Val Pro Ala Leu Asn Arg Thr Gly Asp Pro Gly Pro Gly Pro Ser Ile
             1                   5                       10

CAG AAA ACC TAT GAC CTC ACC CGC TAC CTG GAG CAC CAA CTC CGC AGC         257
Gln Lys Thr Tyr Asp Leu Thr Arg Tyr Leu Glu His Gln Leu Arg Ser
     15                  20                  25

TTG GCT GGG ACC TAT CTG AAC TAC CTG GGC CCC CCT TTC AAC GAG CCA         305
Leu Ala Gly Thr Tyr Leu Asn Tyr Leu Gly Pro Pro Phe Asn Glu Pro
 30                  35                  40                  45

GAC TTC AAC CCT CCC CGC CTG GGG GCA GAG ACT CTG CCC AGG GCC ACT         353
Asp Phe Asn Pro Pro Arg Leu Gly Ala Glu Thr Leu Pro Arg Ala Thr
                 50                  55                  60

GTT GAC TTG GAG GTG TGG CGA AGC CTC AAT GAC AAA CTG CGG CTG ACC         401
Val Asp Leu Glu Val Trp Arg Ser Leu Asn Asp Lys Leu Arg Leu Thr
                 65                  70                  75

CAG AAC TAC GAG GCC TAC AGC CAC CTT CTG TGT TAC TTG CGT GGC CTC         449
Gln Asn Tyr Glu Ala Tyr Ser His Leu Leu Cys Tyr Leu Arg Gly Leu
         80                  85                  90

AAC CGT CAG GCT GCC ACT GCT GAG CTG CGC CGC AGC CTG GCC CAC TTC         497
Asn Arg Gln Ala Ala Thr Ala Glu Leu Arg Arg Ser Leu Ala His Phe
     95                  100                 105

TGC ACC AGC CTC CAG GGC CTG CTG GGC AGC ATT GCG GGC GTC ATG GCA         545
Cys Thr Ser Leu Gln Gly Leu Leu Gly Ser Ile Ala Gly Val Met Ala
110                 115                 120                 125

GCT CTG GGC TAC CCA CTG CCC CAG CCG CTG CCT GGG ACT GAA CCC ACT         593
Ala Leu Gly Tyr Pro Leu Pro Gln Pro Leu Pro Gly Thr Glu Pro Thr
                130                 135                 140

TGG ACT CCT GGC CCT GCC CAC AGT GAC TTC CTC CAG AAG ATG GAC GAC         641
Trp Thr Pro Gly Pro Ala His Ser Asp Phe Leu Gln Lys Met Asp Asp
                145                 150                 155

TTC TGG CTG CTG AAG GAG CTG CAG ACC TGG CTG TGG CGC TCG GCC AAG         689
Phe Trp Leu Leu Lys Glu Leu Gln Thr Trp Leu Trp Arg Ser Ala Lys
        160                 165                 170

GAC TTC AAC CGG CTC AAG AAG AAG ATG CAG CCT CCA GCA GCT GCA GTC         737
Asp Phe Asn Arg Leu Lys Lys Lys Met Gln Pro Pro Ala Ala Ala Val
        175                 180                 185

ACC CTG CAC CTG GGG GCT CAT GGC TTC TGACTTCTGA CCTTCTCCTC              784
Thr Leu His Leu Gly Ala His Gly Phe
190             195

TTCGCTCCCC CCC                                                           797
```

( 2 ) INFORMATION FOR SEQ ID NO:2:

( i ) SEQUENCE CHARACTERISTICS:
( A ) LENGTH: 225 amino acids
( B ) TYPE: amino acid
( D ) TOPOLOGY: linear ( i i ) MOLECULE TYPE: protein ( x i ) SEQUENCE DESCRIPTION: SEQ ID NO:2:

| | | | | | | | | | | | | | |
|---|---|---|---|---|---|---|---|---|---|---|---|---|---|
| Met<br>-27 | Asp | Leu<br>-25 | Arg | Ala | Gly | Asp | Ser<br>-20 | Trp | Gly | Met | Leu | Ala<br>-15 | Cys | Leu | Cys |
| Thr | Val<br>-10 | Leu | Trp | His | Leu | Pro<br>-5 | Ala | Val | Pro | Ala | Leu<br>1 | Asn | Arg | Thr | Gly<br>5 |
| Asp | Pro | Gly | Pro<br>10 | Gly | Pro | Ser | Ile | Gln | Lys<br>15 | Thr | Tyr | Asp | Leu | Thr<br>20 | Arg |
| Tyr | Leu | Glu | His<br>25 | Gln | Leu | Arg | Ser | Leu | Ala<br>30 | Gly | Thr | Tyr | Leu<br>35 | Asn | Tyr |
| Leu | Gly | Pro<br>40 | Pro | Phe | Asn | Glu | Pro<br>45 | Asp | Phe | Asn | Pro | Pro<br>50 | Arg | Leu | Gly |
| Ala | Glu<br>55 | Thr | Leu | Pro | Arg | Ala<br>60 | Thr | Val | Asp | Leu | Glu<br>65 | Val | Trp | Arg | Ser |
| Leu<br>70 | Asn | Asp | Lys | Leu | Arg<br>75 | Leu | Thr | Gln | Asn | Tyr<br>80 | Glu | Ala | Tyr | Ser | His<br>85 |
| Leu | Leu | Cys | Tyr | Leu<br>90 | Arg | Gly | Leu | Asn | Arg<br>95 | Gln | Ala | Ala | Thr | Ala<br>100 | Glu |
| Leu | Arg | Arg | Ser<br>105 | Leu | Ala | His | Phe | Cys<br>110 | Thr | Ser | Leu | Gln | Gly<br>115 | Leu | Leu |
| Gly | Ser | Ile<br>120 | Ala | Gly | Val | Met | Ala<br>125 | Ala | Leu | Gly | Tyr | Pro<br>130 | Leu | Pro | Gln |
| Pro | Leu<br>135 | Pro | Gly | Thr | Glu | Pro<br>140 | Thr | Trp | Thr | Pro | Gly<br>145 | Pro | Ala | His | Ser |
| Asp<br>150 | Phe | Leu | Gln | Lys | Met<br>155 | Asp | Asp | Phe | Trp | Leu<br>160 | Leu | Lys | Glu | Leu | Gln<br>165 |
| Thr | Trp | Leu | Trp | Arg<br>170 | Ser | Ala | Lys | Asp | Phe<br>175 | Asn | Arg | Leu | Lys<br>180 | Lys | Lys |
| Met | Gln | Pro | Pro<br>185 | Ala | Ala | Ala | Val | Thr<br>190 | Leu | His | Leu | Gly<br>195 | Ala | His | Gly |
| Phe | | | | | | | | | | | | | | | |

( 2 ) INFORMATION FOR SEQ ID NO:3:

( i ) SEQUENCE CHARACTERISTICS:
        ( A ) LENGTH: 5087 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 137..138
        ( D ) OTHER INFORMATION: /product="INTERVENING UNSEQUENCED
            REGION OF 1KB"

( x i ) SEQUENCE DESCRIPTION: SEQ ID NO:3:

```
AACCTGCGAG TGGGCCTGGC GGATGGGATT ATTAAAGCTT CGCCGGAGCC GCGGCTCGCC      60

CTCCCACTCC GCCAGCCTCC GGGAGAGGAG CCGCACCCGG CCGGCCCAGC CCCAGCCCCA     120

TGGACCTCCG AGCAGGTTGA AAACCCAAAC TAGCCCTGCT CTTCATAACA TGACAAGCAG     180

CGCCCCATCT GATACCTAAA CCGACCAAGT CACAGCCCTC CAACTCACCC TCTGCCTGCC     240

CAGACCTCAC ACATCCTTG TGGACTCAAA CCTCAACCGC ACTAAATCAA CCAAATCCCA     300

AGTCTAAACT AATCTGAAAC TTTTAAAGTA ACCCAGTCCT TAAACCTAAC CTAGCCCAAT     360

GCCAATTATA TCTACCCTAG CCAAACCCTA ACTGCCTTTG CCAGTCCAAA GTGTCCACTG     420

AATCCTCACC TTGGTCCTCA CTGAAAATCC CAGAAAAGCA TATTTCCCCA CTGCCCACAT     480

CCCTCCTTAC AGCACCCAAC CCTGGCCTCT GGACTCCTGG TATCCTGGGA TGTCCAAACT     540
```

| | | | | | | |
|---|---|---|---|---|---|---|
| CTGCAGTGCC | ATCAGCCAAC | AAGCCCGACT | CGTCAAATGC | ACCTCTCTCC | CTTCCTGTCC | 600 |
| CCACCCTTGC | AGGCTGATGG | AAAGGCCTCA | TTGAAGTCCA | ACTTTTCCCC | ACCTAACACC | 660 |
| AAGAACGGGG | TGAACCTCCA | CACTGCCACC | GTTCCTGAG | AGTGAGCACT | AAATCTCCTT | 720 |
| CAATCTAACC | CCACCCTACA | CTTCCCACAC | TCAGGAATCA | CATCCTAGAA | TATACCCAAA | 780 |
| ACTAAGCCCC | ATAAGGCAGC | CCGACCCTAG | TGGTCTAACC | CTATACCTTG | CTTCCTATGG | 840 |
| GTGAGTCTGT | TCTTGGCGGC | CGCCTCTCTC | CTGCTTCCTC | CCTTAGAGCT | GACTGTGCTC | 900 |
| AGCCTGCCAG | CTCTGACATG | TGCTGTCTCC | CACCCTCTGA | CTCCCCTCAA | GCTGCAGTGG | 960 |
| GACTGGAAGA | CTGGCAGGAA | GCTAGGGTAC | AACTGGAACA | CAGGCAGGTC | GACCTGCAGT | 1020 |
| CCCTAGGCCT | GGCCCCGTCC | CTCCATGTAC | ACACATATAC | ATGTTGGCAC | ACACACAGTG | 1080 |
| GCACACATGC | CAAAGACTCT | CTCAGCTGAC | ACACAGATCC | ATTCTCAAGT | ATCTACTGAT | 1140 |
| AGACACTCAT | GCGTGCCAAG | TCCTCATCCT | CAAACATACA | CATGCCTCTC | TTTCTCTCCC | 1200 |
| GTCTTGCCAG | GAGTGTTTCC | CCTCCTCCAT | CCCCTCTGCC | TCCATCTGG | TGTCCCACCC | 1260 |
| TCACCCCCCA | CCCAGCCCAA | GGTGGGGACA | GACACCTGAG | GGGCTGCCAG | CTGCTTCCCC | 1320 |
| GTGTGGGCCC | GGGCCGCGCT | CATGCTTCTC | GTCCATCCTG | CCCACAGGGG | ACTCGTGGGG | 1380 |
| GATGTTAGCG | TGCCTGTGCA | CGGTGCTCTG | GCACCTCCCT | GCAGTGCCAG | CTCTCAATCG | 1440 |
| CACAGGGGAC | CCAGGGCCTG | GCCCCTCCAT | CCAGAAAACC | TATGACCTCA | CCCGCTACCT | 1500 |
| GGAGCACCAA | CTCCGCAGCT | TGGCTGGGAC | CTATGTGAGT | ATCCAGCGTA | GGAATCTGGG | 1560 |
| AGTTGGGGAG | GAGTGAGGAG | TTGGGGAAAG | ACAGTCCTAA | CCGTGGAGGG | TTCTGGTAAA | 1620 |
| TGATGGGGTG | AGGAGGGGCT | CTTTGGCTCC | CACCAGTCCC | CCTGTCTGGT | CTATCTCCTG | 1680 |
| CCCTTCCCTC | TTAGGTGGCC | CCCCACTTC | CCCATCCCTG | GCCCCAGGAC | TAGGCATGTG | 1740 |
| GGCAGGCCTC | GCACCCGCCT | TGGCCCATTG | CCCCACTGGC | TGCCAGCCCA | GCCGCCCGCC | 1800 |
| TCCCCCTGGG | GGCCGGGGAA | GTCTCCTCTG | TTTACACCGT | GTTGTGGTGT | CTCTTGCGCG | 1860 |
| GGCGGGGTTG | GGTGGGACA | GAGGGGCCCC | ACCTCCCATG | CCTGCGTTCC | AGCTCGCCTC | 1920 |
| TGCCCCCAGA | CCTGGGCCC | TGCTGCTCTG | GACCCAGGGG | CCTCCCTTCC | GTCTGCCTCT | 1980 |
| CCCATCCTAG | CTGGGCCTCC | TAGGGGGGTC | ATGGGGGAAG | GGACTGTAG | GGAACCCAGG | 2040 |
| CAGTAGTGGC | AGGGGGTTTA | GGGTGTGGAT | GGAGGTTATG | CTGTAAGGAT | TTGGGGGTGG | 2100 |
| TCCAGAGGTG | TTCAGAGAGC | CCAGGAGAGA | AGGAAGGAGG | GTTGGAGGAG | CCGAGGCACC | 2160 |
| ATGGGGAACC | GGCCCCCTCT | TCCCGTGTTC | CTCTTCCACA | TCCCAGACCC | TACTCTGGAG | 2220 |
| CCAGGGAAAG | AAAAGGGAAG | AAGGTGGCGG | GGGAGCTGGC | TCCAGCCCCA | GGATACACCG | 2280 |
| AGGAAATTAG | TTTGTCTCTG | TGCTTGTCAG | CGTGTGAACC | TCCCCCTGGG | CCCTTGCCTA | 2340 |
| TCCCAGGCCT | CTCCCCTTGC | TTCTCCCTTC | TTTCCCAGTT | ATACATCTCC | CTCATCCCTT | 2400 |
| TCCCTGGGCC | CCAGCCGCTC | CCCCGAGGGT | TGGAAAGGGC | TCTGCCCTCT | TCCCTATACC | 2460 |
| ATGCTGTCTT | CCATAGCCTT | CCTCCTGTCC | TACTCATGAG | ACTGCCTCCA | TTTCTTCCTT | 2520 |
| CTGCAACCCT | GCTCCTATCA | GCTGAACCCT | TCTTTCGGAG | TGTTAGTGAG | TACCCGTCTC | 2580 |
| TCCCCAGCCC | CTCAGCTGGT | GGGCCTGGGT | GTGTCAGCGG | CAAATGGGGC | TCTGGTTCCA | 2640 |
| ATGGGCCACT | CTCATCTCTC | TCTTGTTCCT | TGTGCAGAAA | ACCTTTGCTT | CACTCCACTG | 2700 |
| CCCTCTCTAG | TTCCGACCC | TTTTTCTCTC | CTGGCTTTCC | CTGCCAAATT | TCTCCAAGGA | 2760 |
| GTGGTCTACA | CCCTCTGCCT | CCACTTCCTC | TCCACCCACT | CACTTCTTAA | CCCCCTGCAA | 2820 |
| TCTGGCTTCC | AGGCCCCAGC | AATGGTTCTC | TCCAAGGTCG | TCAGGCACCT | CCTTGCCAAG | 2880 |
| CCCGACAGTG | TTTTGAAGGC | TCATTCTCCT | TGCTGTCTGT | TTTGCAGCCA | CACTGCTGAG | 2940 |

```
CGCTGCTGCC TTCTCGAACT CCTCTTCCTT GGTCTCTGCA CTCTCCTGGG CCACCTTCTA      3000
CCTCTCCAGC TCCTCCAGGC TCCTCTTCCT CTCTGTCCTG CCCCACAGC  GGGCACTCTC      3060
CCAAGGTTTG CCCACCCAGC CAATCAGCAC GTCCTTCCTG AGCGTCTTGT GCGTCTCCTC      3120
CTCCTCCTTT TTCTACGCCT CTCCATTGGA GAGCTCACCA CCGCCACTGC TTCAACTGTC      3180
ACCTGCATAC AAATGATATC CTTATTGGAA AAACTCAGGG AGGCCATGAA CAAAGAAGCC      3240
TAGCATGGAG ACAGGGCCAG TGTCAGGGGA CACAAAAAAT AGAAACTTTG GGAGCAGGTA      3300
TCTCCTTGGT GGTGAGCCAG CGGCTCTGCC CTCCTCCTTC CCCATCACCC TCTCCTTTTC      3360
ACAGCTGAAC TACCTGGGCC CCCCTTTCAA CGAGCCAGAC TTCAACCCTC CCGCCTGGG       3420
GGCAGAGACT CTGCCCAGGG CCACTGTTGA CTTGGAGGTG TGGCGAAGCC TCAATGACAA      3480
ACTGCGGCTG ACCAGAACT  ACGAGGCCTA CAGCCACCTT CTGTGTTACT TGCGTGGCCT      3540
CAACCGTCAG GCTGCCACTG CTGAGCTGCG CCGCAGCCTG GCCCACTTCT GCACCAGCCT      3600
CCAGGGCCTG CTGGGCAGCA TTGCGGGCGT CATGGCAGCT CTGGGCTACC CACTGCCCA      3660
GCCGCTGCCT GGGACTGAAC CCACTTGGAC TCCTGGCCCT GCCCACAGTG ACTTCCTCCA      3720
GAAGATGGAC GACTTCTGGC TGCTGAAGGA GCTGCAGACC TGGCTGTGGC GCTCGGCCAA      3780
GGACTTCAAC CGGCTCAAGA AGAAGATGCA GCCTCCAGCA GCTGCAGTCA CCCTGCACCT      3840
GGGGGCTCAT GGCTTCTGAC TTCTGACCTT CTCCTCTTCG CTCCCCCTTC AAACCCTGCT      3900
CCCACTTTGT GAGAGCCAGC CCTGTATGCC AACACCTGTT GAGCCAGGAG ACAGAAGCTG      3960
TGAGCCTCTG GCCCTTTCCT GGACCGGCTG GGCGTGTGAT GCGATCAGCC CTGTCTCCTC      4020
CCCACCTCCC AAAGGTCTAC CGAGCTGGGG AGGAGGTACA GTAGGCCCTG TCCTGTCCTG      4080
TTTCTACAGG AAGTCATGCT CGAGGGAGTG TGAAGTGGTT CAGGTTGGTG CAGAGGCGCT      4140
CATGGCCTCC TGCTTCTTGC CTACCACTTG GCCAGTGCCC ACCCAGCCCC TCAGGTGGCA      4200
CATCTGGAGG GCAGGGGTTG AGGGGCCACC ACCACACATG CCTTTCTGGG GTGAAGCCCT      4260
TTGGCTGCCC CACTCTCCTT GGATGGGTGT TGCTCCCTTA TCCCAAATC  ACTCTATACA      4320
TCCAATTCAG GAAACAAACA TGGTGGCAAT TCTACACAAA AAGAGATGAG ATTAACAGTG      4380
CAGGGTTGGG GTCTGCATTG GAGGTGCCCT ATAAACCAGA AGAGAAAATA CTGAAAGCAC      4440
AGGGGCAGGG ACAGACCAGA CCAGACCCAG GAGTCTCCAA AGCACAGAGT GGCAAACAAA      4500
ACCCGAGCTG AGCATCAGGA CCTTGCCTCG AATTGTCTTC CAGTATTACG GTGCCTCTTC      4560
TCTGCCCCCT TTCCCAGGGT ATCTGTGGGT TGCCAGGCTG GGGAGGGCAA CCATAGCCAC      4620
ACCACAGGAT TTCCTGAAAG TTACAATGC  AGTAGCATTT TGGGGTGTAG GGTGGCAGCT      4680
CCCCAAGGCC CTGCCCCCA  GCCCCACCCA CTCATGACTC TAAGTGTGTT GTATTAATAT      4740
TTATTTATTT GGAGATGTTA TTTATTAGAT GATATTTATT GCAGAATTTC TATTCTTGTA      4800
TTAACAAATA AAATGCTTGC CCCAGAACTT AGTCTCTTTG CCCAGCCTCA CCCCTCCTGG      4860
TGCTCATCAG ACTCTTGCCA CCCCTGGCTC CCACTCCCTG CTTGCCTCTG GTGGAGCTGC      4920
ACAGAGCTCT GGGAAGAGGC CCTCTTCCTC CCCGCACTGG GGCGATGGGC GCACCTCAGA      4980
CTTACCCACT GCTGCTGCCA CCACCAACCC CTTGATCCCT CAGTCCTCCC ACACAGCTTC      5040
TGTCCACCCC AGGTTTCCCT CACCCCACCT TTGCTAAGTC TTCCTCA                    5087
```

( 2 ) INFORMATION FOR SEQ ID NO:4:

( i ) SEQUENCE CHARACTERISTICS:
        ( A ) LENGTH: 819 base pairs
        ( B ) TYPE: nucleic acid
        ( C ) STRANDEDNESS: single (D) TOPOLOGY: linear (ii) MOLECULE TYPE: cDNA (ix) FEATURE:
  (A) NAME/KEY: CDS
  (B) LOCATION: 95..769

(ix) FEATURE:
  (A) NAME/KEY: mat_peptide
  (B) LOCATION: 176..769

(ix) FEATURE:
  (A) NAME/KEY: sig_peptide
  (B) LOCATION: 95..175

(xi) SEQUENCE DESCRIPTION: SEQ ID NO:4:

```
TATTATTAAA GCTTCGCCGG AGCCGCGGCT CGCCCTCCCA CTCCGCCAGC CTCTGGGAGA      60

GGAGCCGCGC CCGGCCGGCC CGGCCCCCAG CCCC ATG GAC CTC CGA GCA GGG        112
                                     Met Asp Leu Arg Ala Gly
                                      -27         -25

GAC TCG TGG GGG ATG TTA GCT TGC CTA TGC ACG GTG CTG TGG CAC CTC      160
Asp Ser Trp Gly Met Leu Ala Cys Leu Cys Thr Val Leu Trp His Leu
    -20              -15                  -10

CCT GCA GTG CCA GCT CTT AAT CGC ACA GGA GAT CCA GGC CCT GGC CCC      208
Pro Ala Val Pro Ala Leu Asn Arg Thr Gly Asp Pro Gly Pro Gly Pro
 -5              1                   5                      10

TCC ATC CAG AAA ACC TAT GAC CTC ACC CGC TAC CTG GAG CAT CAA CTC      256
Ser Ile Gln Lys Thr Tyr Asp Leu Thr Arg Tyr Leu Glu His Gln Leu
             15                      20                  25

CGC AGC TTA GCT GGG ACC TAC CTG AAC TAC CTG GGG CCC CCT TTC AAC      304
Arg Ser Leu Ala Gly Thr Tyr Leu Asn Tyr Leu Gly Pro Pro Phe Asn
         30                      35                  40

GAG CCT GAC TTC AAT CCT CCT CGA CTG GGG GCA GAA ACT CTG CCC AGG      352
Glu Pro Asp Phe Asn Pro Pro Arg Leu Gly Ala Glu Thr Leu Pro Arg
     45                  50                  55

GCC ACG GTC AAC TTG GAA GTG TGG CGA AGC CTC AAT GAC AGG CTG CGG      400
Ala Thr Val Asn Leu Glu Val Trp Arg Ser Leu Asn Asp Arg Leu Arg
 60                  65                  70                  75

CTG ACC CAG AAC TAT GAG GCG TAC AGT CAC CTC CTG TGT TAC TTG CGT      448
Leu Thr Gln Asn Tyr Glu Ala Tyr Ser His Leu Leu Cys Tyr Leu Arg
                 80              85                      90

GGC CTC AAC CGT CAG GCT GCC ACA GCT GAA CTC CGA CGT AGC CTG GCC      496
Gly Leu Asn Arg Gln Ala Ala Thr Ala Glu Leu Arg Arg Ser Leu Ala
             95                  100                 105

CAC TTC TGT ACC AGC CTC CAG GGC CTG CTG GGC AGC ATT GCA GGT GTC      544
His Phe Cys Thr Ser Leu Gln Gly Leu Leu Gly Ser Ile Ala Gly Val
         110                 115                 120

ATG GCG ACG CTT GGC TAC CCA CTG CCC CAG CCT CTG CCA GGG ACT GAG      592
Met Ala Thr Leu Gly Tyr Pro Leu Pro Gln Pro Leu Pro Gly Thr Glu
125                 130                 135

CCA GCC TGG GCC CCT GGC CCT GCC CAC AGT GAC TTC CTC CAG AAG ATG      640
Pro Ala Trp Ala Pro Gly Pro Ala His Ser Asp Phe Leu Gln Lys Met
140                 145                 150                 155

GAT GAC TTC TGG CTG CTG AAG GAG CTG CAG ACC TGG CTA TGG CGT TCA      688
Asp Asp Phe Trp Leu Leu Lys Glu Leu Gln Thr Trp Leu Trp Arg Ser
                160                 165                 170

GCC AAG GAC TTC AAC CGG CTT AAG AAG AAG ATG CAG CCT CCA GCA GCT      736
Ala Lys Asp Phe Asn Arg Leu Lys Lys Lys Met Gln Pro Pro Ala Ala
            175                 180                 185

TCA GTC ACC CTG CAC TTG GAG GCA CAT GGT TTC TGACCTCTGA CCCTTAACCC    789
Ser Val Thr Leu His Leu Glu Ala His Gly Phe
        190                 195
```

CCACACCTCC AGGCCCAGTC AGCTGTGCTT                                    819

( 2 ) INFORMATION FOR SEQ ID NO:5:

( i ) SEQUENCE CHARACTERISTICS:
        ( A ) LENGTH: 225 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met -27 | Asp | Leu -25 | Arg | Ala | Gly | Asp | Ser -20 | Trp | Gly | Met | Leu | Ala -15 | Cys | Leu | Cys |
| Thr | Val -10 | Leu | Trp | His | Leu | Pro -5 | Ala | Val | Pro | Ala | Leu | Asn 1 | Arg | Thr | Gly 5 |
| Asp | Pro | Gly | Pro 10 | Gly | Pro | Ser | Ile | Gln | Lys 15 | Thr | Tyr | Asp | Leu | Thr 20 | Arg |
| Tyr | Leu | Glu | His 25 | Gln | Leu | Arg | Ser | Leu 30 | Ala | Gly | Thr | Tyr | Leu 35 | Asn | Tyr |
| Leu | Gly | Pro 40 | Pro | Phe | Asn | Glu | Pro 45 | Asp | Phe | Asn | Pro | Pro 50 | Arg | Leu | Gly |
| Ala | Glu 55 | Thr | Leu | Pro | Arg | Ala 60 | Thr | Val | Asn | Leu | Glu 65 | Val | Trp | Arg | Ser |
| Leu 70 | Asn | Asp | Arg | Leu | Arg 75 | Leu | Thr | Gln | Asn | Tyr 80 | Glu | Ala | Tyr | Ser | His 85 |
| Leu | Leu | Cys | Tyr | Leu 90 | Arg | Gly | Leu | Asn | Arg 95 | Gln | Ala | Ala | Thr | Ala 100 | Glu |
| Leu | Arg | Arg | Ser 105 | Leu | Ala | His | Phe | Cys 110 | Thr | Ser | Leu | Gln | Gly 115 | Leu | Leu |
| Gly | Ser | Ile 120 | Ala | Gly | Val | Met | Ala 125 | Thr | Leu | Gly | Tyr | Pro 130 | Leu | Pro | Gln |
| Pro | Leu 135 | Pro | Gly | Thr | Glu | Pro 140 | Ala | Trp | Ala | Pro | Gly 145 | Pro | Ala | His | Ser |
| Asp 150 | Phe | Leu | Gln | Lys | Met 155 | Asp | Asp | Phe | Trp | Leu 160 | Leu | Lys | Glu | Leu | Gln 165 |
| Thr | Trp | Leu | Trp | Arg 170 | Ser | Ala | Lys | Asp | Phe 175 | Asn | Arg | Leu | Lys | Lys 180 | Lys |
| Met | Gln | Pro | Pro 185 | Ala | Ala | Ser | Val | Thr 190 | Leu | His | Leu | Glu | Ala 195 | His | Gly |
| Phe | | | | | | | | | | | | | | | |

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

AGCAAGCTTC ACCATGGACC TCCGAGCAGG GGACTC                             36

( 2 ) INFORMATION FOR SEQ ID NO:7:

( i ) SEQUENCE CHARACTERISTICS:
        ( A ) LENGTH: 64 base pairs
        ( B ) TYPE: nucleic acid
        ( C ) STRANDEDNESS: single (D) TOPOLOGY: linear (ii) MOLECULE TYPE: other nucleic acid (xi) SEQUENCE DESCRIPTION: SEQ ID NO:7:

```
AGCGGGGCCG CACTACTTGC ATCGTCGCGT CCTTGTACTC GAAGCCATGA GCCCCCAGGT        60

GCAG                                                                    64
```

(2) INFORMATION FOR SEQ ID NO:8:

(i) SEQUENCE CHARACTERISTICS:
        (A) LENGTH: 199 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..178

(ix) FEATURE:
        (A) NAME/KEY: Region
        (B) LOCATION: -21..0

(xi) SEQUENCE DESCRIPTION: SEQ ID NO:8:

```
Met  Asn  Cys  Val  Cys  Arg  Leu  Val  Leu  Val  Val  Leu  Ser  Leu  Trp  Pro
     -20                 -15                      -10

Asp  Thr  Ala  Val  Ala  Pro  Gly  Pro  Pro  Pro  Gly  Pro  Pro  Arg  Val  Ser
-5                        1                   5                        10

Pro  Asp  Pro  Arg  Ala  Glu  Leu  Asp  Ser  Thr  Val  Leu  Leu  Thr  Arg  Ser
               15                     20                       25

Leu  Leu  Ala  Asp  Thr  Arg  Gln  Leu  Ala  Ala  Gln  Leu  Arg  Asp  Lys  Phe
          30                      35                      40

Pro  Ala  Asp  Gly  Asp  His  Asn  Leu  Asp  Ser  Leu  Pro  Thr  Leu  Ala  Met
     45                      50                      55

Ser  Ala  Gly  Ala  Leu  Gly  Ala  Leu  Gln  Leu  Pro  Gly  Val  Leu  Thr  Arg
60                       65                      70                       75

Leu  Arg  Ala  Asp  Leu  Leu  Ser  Tyr  Leu  Arg  His  Val  Gln  Trp  Leu  Arg
               80                      85                      90

Arg  Ala  Gly  Gly  Ser  Ser  Leu  Lys  Thr  Leu  Glu  Pro  Glu  Leu  Gly  Thr
               95                      100                    105

Leu  Gln  Ala  Arg  Leu  Asp  Arg  Leu  Leu  Arg  Arg  Leu  Gln  Leu  Leu  Met
          110                     115                     120

Ser  Arg  Leu  Ala  Leu  Pro  Gln  Pro  Pro  Asp  Pro  Pro  Ala  Pro  Pro
     125                     130                     135

Leu  Ala  Pro  Pro  Ser  Ser  Ala  Trp  Gly  Gly  Ile  Arg  Ala  Ala  His  Ala
140                      145                     150                      155

Ile  Leu  Gly  Gly  Leu  His  Leu  Thr  Leu  Asp  Trp  Ala  Val  Arg  Gly  Leu
                    160                     165                     170

Leu  Leu  Leu  Lys  Thr  Arg  Leu
               175
```

(2) INFORMATION FOR SEQ ID NO:9:

(i) SEQUENCE CHARACTERISTICS:
        (A) LENGTH: 212 amino acids
        (B) TYPE: amino acid
        (C) STRANDEDNESS: single
        (D) TOPOLOGY: linear (ii) MOLECULE TYPE: protein ( i x ) FEATURE:
  ( A ) NAME/KEY: Protein
  ( B ) LOCATION: 1..182

( i x ) FEATURE:
  ( A ) NAME/KEY: Region
  ( B ) LOCATION: -30..0

( x i ) SEQUENCE DESCRIPTION: SEQ ID NO:9:

| Met | Asn | Ser | Phe | Ser | Thr | Ser | Ala | Phe | Gly | Pro | Val | Ala | Phe | Ser | Leu |
|---|---|---|---|---|---|---|---|---|---|---|---|---|---|---|---|
| -30 | | | | | -25 | | | | -20 | | | | | | -15 |
| Gly | Leu | Leu | Leu | Val | Leu | Pro | Ala | Ala | Phe | Pro | Ala | Pro | Val | Pro | Pro |
| | | | | -10 | | | | | -5 | | | | | 1 | |
| Gly | Glu | Asp | Ser | Lys | Asp | Val | Ala | Ala | Pro | His | Arg | Gln | Pro | Leu | Thr |
| | | 5 | | | | | | 10 | | | | 15 | | | |
| Ser | Ser | Glu | Arg | Ile | Asp | Lys | Gln | Ile | Arg | Tyr | Ile | Leu | Asp | Gly | Ile |
| | 20 | | | | | 25 | | | | | 30 | | | | |
| Ser | Ala | Leu | Arg | Lys | Glu | Thr | Cys | Asn | Lys | Ser | Asn | Met | Cys | Glu | Ser |
| 35 | | | | | 40 | | | | | 45 | | | | | 50 |
| Ser | Lys | Glu | Ala | Leu | Ala | Glu | Asn | Asn | Leu | Asn | Leu | Pro | Lys | Met | Ala |
| | | | | | 55 | | | | 60 | | | | | 65 | |
| Glu | Lys | Asp | Gly | Cys | Phe | Gln | Ser | Gly | Phe | Asn | Glu | Glu | Thr | Cys | Leu |
| | | | 70 | | | | | 75 | | | | | 80 | | |
| Val | Lys | Ile | Ile | Thr | Gly | Leu | Leu | Glu | Phe | Glu | Val | Tyr | Leu | Glu | Tyr |
| | | | 85 | | | | | 90 | | | | 95 | | | |
| Leu | Gln | Asn | Arg | Phe | Glu | Ser | Ser | Glu | Glu | Gln | Ala | Arg | Ala | Val | Gln |
| | 100 | | | | | 105 | | | | | 110 | | | | |
| Met | Ser | Thr | Lys | Val | Leu | Ile | Gln | Phe | Leu | Gln | Lys | Lys | Ala | Lys | Asn |
| 115 | | | | | 120 | | | | 125 | | | | | | 130 |
| Leu | Asp | Ala | Ile | Thr | Thr | Pro | Asp | Pro | Thr | Thr | Asn | Ala | Ser | Leu | Leu |
| | | | | 135 | | | | | 140 | | | | | 145 | |
| Thr | Lys | Leu | Gln | Ala | Gln | Asn | Gln | Trp | Leu | Gln | Asp | Met | Thr | Thr | His |
| | | | | 150 | | | | 155 | | | | | 160 | | |
| Leu | Ile | Leu | Arg | Ser | Phe | Lys | Glu | Phe | Leu | Gln | Ser | Ser | Leu | Arg | Ala |
| | | | 165 | | | | 170 | | | | | 175 | | | |
| Leu | Arg | Gln | Met | | | | | | | | | | | | |
| | | | 180 | | | | | | | | | | | | |

( 2 ) INFORMATION FOR SEQ ID NO:10:

( i ) SEQUENCE CHARACTERISTICS:
  ( A ) LENGTH: 204 amino acids
  ( B ) TYPE: amino acid
  ( C ) STRANDEDNESS: single
  ( D ) TOPOLOGY: linear ( i i ) MOLECULE TYPE: protein ( i x ) FEATURE:
  ( A ) NAME/KEY: Protein
  ( B ) LOCATION: 1..174

( i x ) FEATURE:
  ( A ) NAME/KEY: Region
  ( B ) LOCATION: -30..0

( x i ) SEQUENCE DESCRIPTION: SEQ ID NO:10:

| Met | Ala | Gly | Pro | Ala | Thr | Gln | Ser | Pro | Met | Lys | Leu | Met | Ala | Leu | Gln |
|---|---|---|---|---|---|---|---|---|---|---|---|---|---|---|---|
| -30 | | | | | -25 | | | | -20 | | | | | | -15 |
| Leu | Leu | Leu | Trp | His | Ser | Ala | Leu | Trp | Thr | Val | Gln | Glu | Ala | Thr | Pro |
| | | | | -10 | | | | -5 | | | | | | 1 | |

| | | | | | | | | | | | | | | | |
|---|---|---|---|---|---|---|---|---|---|---|---|---|---|---|---|
|Leu|Gly|Pro|Ala|Ser|Ser|Leu|Pro|Gln|Ser|Phe|Leu|Leu|Lys|Cys|Leu|
| |  |5 | | | |  |10| | |  |  |  |15|  |  |
|Glu|Gln|Val|Arg|Lys|Ile|Gln|Gly|Asp|Gly|Ala|Ala|Leu|Gln|Glu|Lys|
| |  |20 | | | |25| |  | |30|  |  |  |  |  |
|Leu|Cys|Ala|Thr|Tyr|Lys|Leu|Cys|His|Pro|Glu|Leu|Val|Leu|Leu| |
|35|  |  |  |  |40| |  |  |  |45|  |  |  |50|  |
|Gly|His|Ser|Leu|Gly|Ile|Pro|Trp|Ala|Pro|Leu|Ser|Ser|Cys|Pro|Ser|
| |  |  |  |55| |  |  |  |60|  |  |  |  |65|  |
|Gln|Ala|Leu|Gln|Leu|Ala|Gly|Cys|Leu|Ser|Gln|Leu|His|Ser|Gly|Leu|
| |  |  |70| | |  |  |75|  |  |  |  |80|  |  |
|Phe|Leu|Tyr|Gln|Gly|Leu|Leu|Gln|Ala|Leu|Glu|Gly|Ile|Ser|Pro|Glu|
| |  |85 | | | |  |90|  |  |  |  |95|  |  |  |
|Leu|Gly|Pro|Thr|Leu|Asp|Thr|Leu|Gln|Leu|Asp|Val|Ala|Asp|Phe|Ala|
| |  |100| | | |105| |  |  |  |110| | |  |  |
|Thr|Thr|Ile|Trp|Gln|Gln|Met|Glu|Glu|Leu|Gly|Met|Ala|Pro|Ala|Leu|
|115| | |  |  |120| |  |  |  |125| | |  |  |130|
|Gln|Pro|Thr|Gln|Gly|Ala|Met|Pro|Ala|Phe|Ala|Ser|Ala|Phe|Gln|Arg|
| |  |  |  |135| |  |  |  |140| |  |  |  |145|  |
|Arg|Ala|Gly|Gly|Val|Leu|Val|Ala|Ser|His|Leu|Gln|Ser|Phe|Leu|Glu|
| |  |  |150| | |  |  |  |155| |  |  |160|  |  |
|Val|Ser|Tyr|Arg|Val|Leu|Arg|His|Leu|Ala|Gln|Pro| | | | |
| |  |  |165| | |  |170| | |  |  | | | | |

( 2 ) INFORMATION FOR SEQ ID NO:11:

( i ) SEQUENCE CHARACTERISTICS:
      ( A ) LENGTH: 201 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:11:

| | | | | | | | | | | | | | | | |
|---|---|---|---|---|---|---|---|---|---|---|---|---|---|---|---|
|Met|Ser|Arg|Arg|Glu|Gly|Ser|Leu|Glu|Asp|Pro|Gln|Thr|Asp|Ser|Ser|
|1 |  |  |  |5 |  |  |  |  |10|  |  |  |  |15|  |
|Val|Ser|Leu|Leu|Pro|His|Leu|Glu|Ala|Lys|Ile|Arg|Gln|Thr|His|Ser|
| |  |  |20| | |  |  |  |25|  |  |  |30|  |  |
|Leu|Ala|His|Leu|Leu|Thr|Lys|Tyr|Ala|Glu|Gln|Leu|Leu|Gln|Glu|Tyr|
| |  |35 | | | |40| |  |  |  |  |45|  |  |  |
|Val|Gln|Leu|Gln|Gly|Asp|Pro|Phe|Gly|Leu|Pro|Ser|Phe|Ser|Pro|Pro|
| |  |50 | | |55| |  |  |  |  |60|  |  |  |  |
|Arg|Leu|Pro|Val|Ala|Gly|Leu|Ser|Ala|Pro|Ala|Pro|Ser|His|Ala|Gly|
|65|  |  |  |  |70|  |  |  |75|  |  |  |  |  |80|
|Leu|Pro|Val|His|Glu|Arg|Leu|Arg|Leu|Asp|Ala|Ala|Leu|Ala|Ala|Ala|
| |  |  |  |85| |  |  |  |90|  |  |  |  |95|  |
|Leu|Pro|Pro|Leu|Leu|Asp|Ala|Val|Cys|Arg|Arg|Gln|Ala|Glu|Leu|Asn|
| |  |  |100| | |  |  |105| |  |  |  |110| | |
|Pro|Arg|Ala|Pro|Arg|Leu|Leu|Arg|Arg|Leu|Glu|Asp|Ala|Ala|Arg|Gln|
| |  |115| | | |  |  |120| |  |  |  |125| | |
|Ala|Arg|Ala|Leu|Gly|Ala|Ala|Val|Glu|Ala|Leu|Leu|Ala|Ala|Leu|Gly|
| |  |130| | | |  |135| |  |  |  |140| | | |
|Ala|Ala|Asn|Arg|Gly|Pro|Arg|Ala|Glu|Pro|Pro|Ala|Ala|Thr|Ala|Ser|
|145| | |  |  |150| |  |  |  |155| |  |  |  |160|
|Ala|Ala|Ser|Ala|Thr|Gly|Val|Phe|Pro|Ala|Lys|Val|Leu|Gly|Leu|Arg|
| |  |  |  |165| |  |  |  |170| | |  |  |  |175|
|Val|Cys|Gly|Leu|Tyr|Arg|Glu|Trp|Leu|Ser|Arg|Thr|Glu|Gly|Asp|Leu|

|     |     | 180 |     |     |     | 185 |     |     |     | 190 |     |     |     |
| --- | --- | --- | --- | --- | --- | --- | --- | --- | --- | --- | --- | --- | --- |

Gly Gln Leu Leu Pro Gly Gly Ser Ala
     195                     200

(2) INFORMATION FOR SEQ ID NO:12:

(i) SEQUENCE CHARACTERISTICS:
        (A) LENGTH: 199 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Met Ala Phe Thr Glu His Pro Leu Thr Pro His Arg Arg Asp Leu Cys
1               5                   10                  15

Ser Arg Ser Ile Trp Leu Ala Arg Lys Ile Arg Ser Asp Leu Thr Ala
            20                  25                  30

Leu Thr Glu Ser Tyr Val Lys His Gln Gly Leu Asn Lys Asn Ile Asn
        35                  40                  45

Leu Asp Ser Ala Asp Gly Met Pro Val Ala Ser Thr Asp Gln Trp Ser
    50                  55                  60

Glu Leu Thr Glu Ala Glu Arg Leu Gln Glu Asn Leu Gln Ala Tyr Arg
65                  70                  75                  80

Thr Phe His Val Leu Leu Ala Arg Leu Leu Glu Asp Gln Gln Val His
                85                  90                  95

Phe Thr Pro Thr Glu Gly Asp Phe His Gln Ala Ile His Thr Leu Leu
            100                 105                 110

Leu Gln Val Ala Ala Phe Ala Tyr Gln Ile Glu Glu Leu Met Ile Leu
        115                 120                 125

Leu Glu Tyr Lys Ile Pro Arg Asn Glu Ala Asp Gly Met Pro Ile Asn
    130                 135                 140

Val Gly Asp Gly Gly Leu Phe Glu Lys Lys Leu Trp Gly Leu Lys Val
145                 150                 155                 160

Leu Gln Glu Leu Ser Gln Trp Thr Val Arg Ser Ile His Asp Leu Arg
                165                 170                 175

Phe Ile Ser Ser His Gln Thr Gly Ile Pro Ala Arg Gly Ser His Tyr
            180                 185                 190

Ile Ala Asn Asn Lys Lys Met
        195

(2) INFORMATION FOR SEQ ID NO:13:

(i) SEQUENCE CHARACTERISTICS:
        (A) LENGTH: 252 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..227

(ix) FEATURE:
        (A) NAME/KEY: Region
        (B) LOCATION: -25..0

(xi) SEQUENCE DESCRIPTION: SEQ ID NO:13:

Met Gly Val Leu Leu Thr Gln Arg Thr Leu Leu Ser Leu Val Leu Ala
-25                 -20                 -15                 -10

| Leu | Leu | Phe | Pro | Ser<br>-5 | Met | Ala | Ser | Met | Ala<br>1 | Ala | Ile | Gly | Ser<br>5 | Cys | Ser |

| Lys | Glu | Tyr | Arg | Val | Leu | Leu | Gly | Gln | Leu | Gln | Lys | Gln | Thr | Asp | Leu |
| | | | 10 | | | | 15 | | | | 20 | | | | |

| Met | Gln | Asp | Thr | Ser | Arg | Leu | Leu | Asp | Pro | Tyr | Ile | Arg | Ile | Gln | Gly |
| | 25 | | | | 30 | | | | | | 35 | | | | |

| Leu | Asp | Val | Pro | Lys | Leu | Arg | Glu | His | Cys | Arg | Glu | Arg | Pro | Gly | Ala |
| 40 | | | | | 45 | | | | | 50 | | | | | 55 |

| Phe | Pro | Ser | Glu | Glu | Thr | Leu | Arg | Gly | Leu | Gly | Arg | Arg | Gly | Phe | Leu |
| | | | | 60 | | | | | 65 | | | | | 70 | |

| Gln | Thr | Leu | Asn | Ala | Thr | Leu | Gly | Cys | Val | Leu | His | Arg | Leu | Ala | Asp |
| | | | 75 | | | | | 80 | | | | | 85 | | |

| Leu | Glu | Gln | Arg | Leu | Pro | Lys | Ala | Gln | Asp | Leu | Glu | Arg | Ser | Gly | Leu |
| | | 90 | | | | | 95 | | | | | 100 | | | |

| Asn | Ile | Glu | Asp | Leu | Glu | Lys | Leu | Gln | Met | Ala | Arg | Pro | Asn | Ile | Leu |
| | 105 | | | | | 110 | | | | | 115 | | | | |

| Gly | Leu | Arg | Asn | Asn | Ile | Tyr | Cys | Met | Ala | Gln | Leu | Leu | Asp | Asn | Ser |
| 120 | | | | | 125 | | | | | 130 | | | | | 135 |

| Asp | Thr | Ala | Glu | Pro | Thr | Lys | Ala | Gly | Arg | Gly | Ala | Ser | Gln | Pro | Pro |
| | | | | 140 | | | | | 145 | | | | | 150 | |

| Thr | Pro | Thr | Pro | Ala | Ser | Asp | Ala | Phe | Gln | Arg | Lys | Leu | Glu | Gly | Cys |
| | | | 155 | | | | | 160 | | | | | 165 | | |

| Arg | Phe | Leu | His | Gly | Tyr | His | Arg | Phe | Met | His | Ser | Val | Gly | Arg | Val |
| | | | 170 | | | | | 175 | | | | | 180 | | |

| Phe | Ser | Lys | Trp | Gly | Glu | Ser | Pro | Asn | Arg | Ser | Arg | Arg | His | Ser | Pro |
| | | 185 | | | | | 190 | | | | | 195 | | | |

| His | Gln | Ala | Leu | Arg | Lys | Gly | Val | Arg | Arg | Thr | Arg | Pro | Ser | Arg | Lys |
| 200 | | | | | 205 | | | | | 210 | | | | | 215 |

| Gly | Lys | Arg | Leu | Met | Thr | Arg | Gly | Gln | Leu | Pro | Arg |
| | | | | 220 | | | | | 225 | | |

( 2 ) INFORMATION FOR SEQ ID NO:14:

( i ) SEQUENCE CHARACTERISTICS:
        ( A ) LENGTH: 202 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Protein
        ( B ) LOCATION: 1..180

( i x ) FEATURE:
        ( A ) NAME/KEY: Region
        ( B ) LOCATION: -22..0

( x i ) SEQUENCE DESCRIPTION: SEQ ID NO:14:

| Met | Lys | Val | Leu | Ala | Ala | Gly | Val | Val | Pro | Leu | Leu | Leu | Val | Leu | His |
| | | | -20 | | | | | -15 | | | | | -10 | | |

| Trp | Lys | His | Gly | Ala | Gly | Ser | Pro | Leu | Pro | Ile | Thr | Pro | Val | Asn | Ala |
| | -5 | | | | | 1 | | | | 5 | | | | | 10 |

| Thr | Cys | Ala | Ile | Arg | His | Pro | Cys | His | Asn | Asn | Leu | Met | Asn | Gln | Ile |
| | | | | 15 | | | | | 20 | | | | | 25 | |

| Arg | Ser | Gln | Leu | Ala | Gln | Leu | Asn | Gly | Ser | Ala | Asn | Ala | Leu | Phe | Ile |
| | | | | 30 | | | | | 35 | | | | | 40 | |

| Leu | Tyr | Tyr | Thr | Ala | Gln | Gly | Glu | Pro | Phe | Pro | Asn | Asn | Leu | Asp | Lys |

|  |  |  |  | 45 |  |  |  | 50 |  |  |  | 55 |  |  |  |
|---|---|---|---|---|---|---|---|---|---|---|---|---|---|---|---|
| Leu | Cys<br>60 | Gly | Pro | Asn | Val | Thr<br>65 | Asp | Phe | Pro | Pro | Phe<br>70 | His | Ala | Asn | Gly |
| Thr<br>75 | Glu | Lys | Ala | Lys | Leu<br>80 | Val | Glu | Leu | Tyr | Arg<br>85 | Ile | Val | Val | Tyr | Leu<br>90 |
| Gly | Thr | Ser | Leu | Gly<br>95 | Asn | Ile | Thr | Arg | Asp<br>100 | Gln | Lys | Ile | Leu | Asn<br>105 | Pro |
| Ser | Ala | Leu | Ser<br>110 | Leu | His | Ser | Lys | Leu<br>115 | Asn | Ala | Thr | Ala | Asp<br>120 | Ile | Leu |
| Arg | Gly | Leu<br>125 | Leu | Ser | Asn | Val | Leu<br>130 | Cys | Arg | Leu | Cys | Ser<br>135 | Lys | Tyr | His |
| Val | Gly<br>140 | His | Val | Asp | Val | Thr<br>145 | Tyr | Gly | Pro | Asp | Thr<br>150 | Ser | Gly | Lys | Asp |
| Val<br>155 | Phe | Gln | Lys | Lys | Lys<br>160 | Leu | Gly | Cys | Gln | Leu<br>165 | Leu | Gly | Lys | Tyr | Lys<br>170 |
| Gln | Ile | Ile | Ala | Val<br>175 | Leu | Ala | Gln | Ala | Phe<br>180 | | | | | | |

(2) INFORMATION FOR SEQ ID NO:15:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:15:

AGCGCTACGG TCGACCCGGC GTTTTTTTT TTTTTTTTT TTACG    45

(2) INFORMATION FOR SEQ ID NO:16:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:16:

GGAAGGAAAA AAGCGGCCGC TACA    24